US012642971B2

(12) United States Patent
Mueller et al.

(10) Patent No.: US 12,642,971 B2
(45) Date of Patent: Jun. 2, 2026

(54) FEEDBACK CONTROL OF ELECTRICAL STIMULATION THERAPY BASED ON ELECTRIC FIELD IMAGING

(71) Applicant: Medtronic, Inc., Minneapolis, MN (US)

(72) Inventors: Jerel K. Mueller, St. Paul, MN (US); Leonid M. Litvak, Bet Shemesh (IL); Vinod Sharma, Maple Grove, MN (US); Katelynn M. Johnson, New Brighton, MN (US); Jiashu Li, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 364 days.

(21) Appl. No.: 18/263,178

(22) PCT Filed: Feb. 23, 2022

(86) PCT No.: PCT/US2022/070796
§ 371 (c)(1),
(2) Date: Jul. 27, 2023

(87) PCT Pub. No.: WO2022/183189
PCT Pub. Date: Sep. 1, 2022

(65) Prior Publication Data
US 2024/0100342 A1      Mar. 28, 2024

Related U.S. Application Data

(60) Provisional application No. 63/153,092, filed on Feb. 24, 2021.

(51) Int. Cl.
*A61N 1/36*      (2006.01)
*A61B 5/00*      (2006.01)
*A61B 5/388*     (2021.01)

(52) U.S. Cl.
CPC .......... *A61N 1/36139* (2013.01); *A61B 5/388* (2021.01); *A61B 5/4836* (2013.01); *A61N 1/3615* (2013.01)

(58) Field of Classification Search
CPC ............ A61N 1/36139; A61N 1/36062; A61N 1/36175; A61N 1/36071; A61N 1/3615;
(Continued)

(56) References Cited

U.S. PATENT DOCUMENTS 5,603,726 A      2/1997 Schulman et al.
5,800,465 A      9/1998 Thompson et al.
(Continued)

FOREIGN PATENT DOCUMENTS

EP      2396072 B1      3/2013
EP      3013413 A1      5/2016
(Continued)

OTHER PUBLICATIONS

"St. Jude's Prodigy Neurostimulator with Burst Technology," Medgadget, Mar. 20, 2014, 4 pp.
(Continued)

*Primary Examiner* — Jon Eric C Morales
(74) *Attorney, Agent, or Firm* — Shumaker & Sieffert, P.A.

(57)      ABSTRACT

Devices, systems, and techniques are described that use electric field imaging (often referred to as the sensed stimulation artifact representative of a delivered stimulus) as an informative feedback signal to provide closed loop control of electrical stimulation therapy. In some examples, the electric field imaging may be used in combination with other feedback signals, such as ECAP do monitor and adjust the delivered electrical stimulation therapy.

20 Claims, 20 Drawing Sheets

(58) Field of Classification Search

CPC ............ A61N 1/36067; A61N 1/36178; A61N 1/36153; A61N 1/36031; A61N 1/36146; A61N 1/36064; A61N 1/36171; A61N 1/36107; A61N 1/36125; A61N 1/0534; A61N 1/0551; A61N 1/36132; A61N 1/025; A61N 1/3606; A61N 1/37247; A61N 1/36135; A61N 1/37235; A61N 1/36034; A61N 1/36192; A61N 1/36185; A61N 1/36007; A61N 1/36128; A61N 1/36167; A61N 1/0456; A61N 1/0476; A61N 1/0484; A61N 1/36014; A61N 1/36057; A61N 1/36157; A61N 1/36082; A61N 1/0553; A61N 1/0504; A61N 1/0531; A61N 1/36085; A61N 1/36114; A61N 1/0556; A61N 1/08; A61N 1/0492; A61N 1/36; A61N 1/36021; A61N 1/36078; A61N 1/3614; A61N 1/36142; A61N 1/36164; A61N 1/3712; A61N 1/372; A61N 2001/083; A61N 1/36003; A61N 1/37205; A61N 1/37241; A61N 1/3605; A61N 1/36196; A61B 5/4836; A61B 5/388; A61B 5/1116; A61B 5/24; A61B 5/686; A61B 5/40; A61B 2562/0219; A61B 5/383; A61B 5/4041; A61B 5/4029; A61B 5/4035; A61B 5/725; A61B 5/7217; A61B 5/316; A61B 5/369; A61B 5/374; A61B 5/4094; A61B 5/4848; A61B 5/7282; A61B 5/0022; A61B 5/02405; A61B 5/0531; A61B 5/08; A61B 5/1114; A61B 5/1118; A61B 5/4082; A61B 5/4809; A61B 5/4815; A61B 5/7264; A61B 5/7475; A61B 5/0031; A61B 5/0205; A61B 5/1107; A61B 5/1113; A61B 5/202; A61B 5/389; A61B 5/391; A61B 5/4052; A61B 5/407; A61B 5/4205; A61B 5/4233; A61B 5/6874; A61B 2562/046; A61B 5/311; G16H 20/40

See application file for complete search history.

(56) References Cited

U.S. PATENT DOCUMENTS

| | | | |
|---|---|---|---|
| 5,855,594 | A | 1/1999 | Olive et al. |
| 6,157,861 | A | 12/2000 | Faltys et al. |
| 6,205,360 | B1 | 3/2001 | Carter |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,076,292 | B2 | 7/2006 | Forsberg |
| 7,206,640 | B1 | 4/2007 | Overstreet |
| 7,333,858 | B2 | 2/2008 | Killian et al. |
| 7,577,480 | B2 | 8/2009 | Zeijlemaker |
| 7,616,999 | B2 | 11/2009 | Overstreet et al. |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 | 9/2010 | Miesel et al. |
| 8,036,747 | B2 | 10/2011 | Thacker et al. |
| 8,090,446 | B2 | 1/2012 | Fowler et al. |
| 8,504,150 | B2 | 8/2013 | Skelton |
| 8,620,441 | B2 | 12/2013 | Greenberg et al. |
| 8,676,329 | B2 | 3/2014 | Wacnik et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,751,009 | B2 | 6/2014 | Wacnik |
| 8,897,888 | B2 | 11/2014 | Parker et al. |
| 8,923,984 | B2 | 12/2014 | Parker et al. |
| 9,002,460 | B2 | 4/2015 | Parker |
| 9,072,910 | B2 | 7/2015 | Parker et al. |
| 9,089,714 | B2 | 7/2015 | Robinson |
| 9,089,715 | B2 | 7/2015 | Parker et al. |
| 9,138,582 | B2 | 9/2015 | Doan et al. |
| 9,155,892 | B2 | 10/2015 | Parker et al. |
| 9,283,373 | B2 | 3/2016 | Parker et al. |
| 9,302,112 | B2 | 4/2016 | Bornzin et al. |
| 9,339,655 | B2 | 5/2016 | Carbunaru |
| 9,364,667 | B1 | 6/2016 | Dinsmoor et al. |
| 9,381,356 | B2 | 7/2016 | Parker et al. |
| 9,386,934 | B2 | 7/2016 | Parker et al. |
| 9,387,325 | B1 | 7/2016 | Min et al. |
| 9,533,148 | B2 | 1/2017 | Carcieri |
| 9,566,439 | B2 | 2/2017 | Single et al. |
| 9,597,507 | B2 | 3/2017 | Johanek et al. |
| 9,700,713 | B2 | 7/2017 | Robinson et al. |
| 9,814,880 | B2 | 11/2017 | Hershey et al. |
| 9,872,990 | B2 | 1/2018 | Parker et al. |
| 9,993,646 | B2 | 6/2018 | Parramon et al. |
| 10,136,832 | B2 | 11/2018 | Liu et al. |
| 10,183,168 | B2 | 1/2019 | Baru et al. |
| 10,569,088 | B2 | 2/2020 | Dinsmoor et al. |
| 10,933,242 | B2 | 3/2021 | Torgerson |
| 11,547,855 | B2 | 1/2023 | Dinsmoor et al. |
| 2004/0267333 | A1 | 12/2004 | Kronberg |
| 2008/0221640 | A1 | 9/2008 | Overstreet et al. |
| 2008/0300655 | A1 | 12/2008 | Cholette |
| 2009/0076560 | A1 | 3/2009 | Bjorling et al. |
| 2010/0198295 | A1 | 8/2010 | Sheldon et al. |
| 2011/0054570 | A1 | 3/2011 | Lane |
| 2011/0071589 | A1 | 3/2011 | Starkebaum et al. |
| 2011/0077712 | A1 | 3/2011 | Killian |
| 2011/0125223 | A1 | 5/2011 | Carbunaru et al. |
| 2012/0155188 | A1 | 6/2012 | Buettner et al. |
| 2013/0208390 | A1 | 8/2013 | Singh et al. |
| 2013/0268021 | A1 | 10/2013 | Moffitt |
| 2013/0289664 | A1 | 10/2013 | Johanek |
| 2013/0289683 | A1 | 10/2013 | Parker et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0243924 | A1 | 8/2014 | Zhu et al. |
| 2014/0243926 | A1 | 8/2014 | Carcieri et al. |
| 2014/0243931 | A1 | 8/2014 | Parker et al. |
| 2014/0277282 | A1 | 9/2014 | Jaax |
| 2014/0288577 | A1 | 9/2014 | Robinson et al. |
| 2014/0293737 | A1 | 10/2014 | Parker et al. |
| 2014/0296936 | A1 | 10/2014 | Alataris et al. |
| 2014/0324143 | A1 | 10/2014 | Robinson et al. |
| 2014/0371813 | A1 | 12/2014 | King et al. |
| 2014/0378941 | A1 | 12/2014 | Su et al. |
| 2014/0379043 | A1 | 12/2014 | Howard |
| 2015/0005842 | A1 | 1/2015 | Lee et al. |
| 2015/0012068 | A1 | 1/2015 | Bradley et al. |
| 2015/0032181 | A1 | 1/2015 | Baynham et al. |
| 2015/0057729 | A1 | 2/2015 | Parker et al. |
| 2015/0127062 | A1 | 5/2015 | Holley et al. |
| 2015/0179177 | A1 | 6/2015 | Nagao |
| 2015/0282725 | A1 | 10/2015 | Single |
| 2015/0313487 | A1 | 11/2015 | Single et al. |
| 2015/0360031 | A1 | 12/2015 | Bornzin et al. |
| 2015/0374999 | A1 | 12/2015 | Parker et al. |
| 2016/0082252 | A1 | 3/2016 | Hershey et al. |
| 2016/0121124 | A1 | 5/2016 | Johanek et al. |
| 2016/0129272 | A1 | 5/2016 | Hou et al. |

(56) References Cited

U.S. PATENT DOCUMENTS

| | | | |
|---|---|---|---|
| 2016/0136420 A1 | 5/2016 | Brink et al. | |
| 2016/0157769 A1 | 6/2016 | Min et al. | |
| 2016/0158550 A1 | 6/2016 | Hou et al. | |
| 2016/0166164 A1 | 6/2016 | Obradovic et al. | |
| 2016/0175594 A1 | 6/2016 | Min et al. | |
| 2016/0206883 A1 | 7/2016 | Bornzin et al. | |
| 2016/0287126 A1 | 10/2016 | Parker et al. | |
| 2016/0287182 A1 | 10/2016 | Single | |
| 2016/0346534 A1 | 12/2016 | Isaacson et al. | |
| 2016/0361542 A1 | 12/2016 | Kaula et al. | |
| 2017/0001017 A9 | 1/2017 | Parker et al. | |
| 2017/0049345 A1 | 2/2017 | Single | |
| 2017/0071490 A1 | 3/2017 | Parker et al. | |
| 2017/0135624 A1 | 5/2017 | Parker | |
| 2017/0173332 A1 | 6/2017 | Overstreet | |
| 2017/0209695 A1 | 7/2017 | Solomon | |
| 2017/0216587 A1 | 8/2017 | Parker | |
| 2017/0216602 A1 | 8/2017 | Waataja et al. | |
| 2017/0296823 A1 | 10/2017 | Hershey et al. | |
| 2017/0361101 A1 | 12/2017 | Single | |
| 2017/0361103 A1 | 12/2017 | Hadjiyski | |
| 2018/0056073 A1 | 3/2018 | Torgerson | |
| 2018/0078769 A1 | 3/2018 | Dinsmoor et al. | |
| 2018/0110987 A1 | 4/2018 | Parker | |
| 2018/0117335 A1 | 5/2018 | Parker et al. | |
| 2018/0126169 A1 | 5/2018 | Hou et al. | |
| 2018/0132760 A1 | 5/2018 | Parker | |
| 2019/0099601 A1 | 4/2019 | Torgerson | |
| 2019/0105496 A1 | 4/2019 | Min et al. | |
| 2019/0209844 A1 | 7/2019 | Esteller et al. | |
| 2019/0366094 A1 | 12/2019 | Esteller et al. | |
| 2019/0388692 A1 | 12/2019 | Dinsmoor et al. | |
| 2019/0388695 A1 | 12/2019 | Dinsmoor et al. | |
| 2020/0171312 A1 | 6/2020 | Dinsmoor et al. | |
| 2020/0171313 A1 | 6/2020 | Dinsmoor et al. | |
| 2020/0188665 A1 | 6/2020 | Annetta et al. | |
| 2020/0305745 A1 | 10/2020 | Wagenbach et al. | |
| 2021/0101007 A1 | 4/2021 | Hamner et al. | |
| 2021/0121698 A1 | 4/2021 | Dinsmoor et al. | |
| 2021/0275817 A1 | 9/2021 | Li | |
| 2022/0096839 A1* | 3/2022 | Hareland | A61N 1/36139 |
| 2022/0323764 A1* | 10/2022 | Esteller | A61N 1/3615 |

FOREIGN PATENT DOCUMENTS

| | | | |
|---|---|---|---|
| EP | 3024540 B1 | 10/2018 | |
| WO | 2002009808 A1 | 2/2002 | |
| WO | 2010058178 A1 | 5/2010 | |
| WO | 2012155188 A1 | 11/2012 | |
| WO | 2014/210373 A1 | 12/2014 | |
| WO | 2015143509 A1 | 10/2015 | |
| WO | 2015179177 A1 | 11/2015 | |
| WO | 2015179281 A2 | 11/2015 | |
| WO | 2016090420 A1 | 6/2016 | |
| WO | 2016090436 A1 | 6/2016 | |
| WO | 2016191808 A1 | 12/2016 | |
| WO | 2017100866 A1 | 6/2017 | |
| WO | 2017106503 A1 | 6/2017 | |
| WO | 2017173493 A1 | 10/2017 | |
| WO | 2017184238 A1 | 10/2017 | |
| WO | 2017219096 A1 | 12/2017 | |
| WO | 2018080753 A1 | 5/2018 | |
| WO | 2018080754 A1 | 5/2018 | |
| WO | 2018106813 A1 | 6/2018 | |
| WO | 2019231794 A1 | 12/2019 | |
| WO | 2020251899 A1 | 12/2020 | |

OTHER PUBLICATIONS

Abejon MD "Back pain coverage with spinal cord stimulation: A different treatment for each patient," International Neuromodulation Society. Jun. 10, 2015; 567, Abstract Only, 1 pp.

Abeloos MD "High density stimulation as an alternative to uncomfortable cervical tonic spinal cord stimulation: case report," International Neuromodulation Society 12th World Congress, Jun. 11-15, 2015, Abstract Only, 1 pp.

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Chakravarthy et al., "Sensing Evoked Compound Action Potentials from the Spinal Cord: Novel Preclinical and Clinical Considerations for the Pain Management Researcher and Clinician", J Pain Res., Dec. 4, 2020, pp. 3269-3279.

Crosby et al., "Modulation of activity and conduction in single dorsal column axons by kilohertz-frequency spinal cord stimulation," American Physiological Society, published online Oct. 19, 2016, 27 pp.

Cuellar MD PhD, et al., "Effect of high-frequency alternating current on spinal afferent nociceptive transmission," Neuromodulation: Technology at the Neural Interface; Jul.-Aug. 2013;16(4): pp. 318-327.

Cui et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder et al., "Burst spinal cord stimulation for limb and back pain," World neurosurgery, Nov. 2013; 80(5):642-649, e641.

De Ridder MD PhD et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak MD et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res., 1313: (2010) available online Dec. 3, 2009 pp. 53-61.

Grider DO/PhD et al., "High Frequency (1000 Hz) Stimulation Using Commercially Available Implantable Pulse Generator," North American Neuromodulation Society. Dec. 2013, Abstract Only, 2 pp.

Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Holsheimer, "Computer modelling of spinal cord stimulation and its contribution to therapeutic efficacy," Spinal Cord Aug. 1998, 36: pp. 531-540.

Hubscher et al., "Convergence and cross talk in urogenital neural circuitries," J. Neurophysiol 110: 1997-2005, first published Aug. 7, 2013, 9 pp.

Hunt et al. "The molecular dynamics of pain control," Nature Reviews Neuroscience, vol. 2, Feb. 2001, pp. 83-91.

International Preliminary Report on Patentability from International Application No. PCT/US2022/070796 dated Sep. 7, 2023, 7 pp.

International Search Report and Written Opinion of International Application No. PCT/US2022/070796, dated Jun. 15, 2022, 12 pp.

Kemler MD et al., "Spinal cord stimulation in patients with chronic reflex sympathetic dystrophy," N Engl J Med, Aug. 31, 2000; 343(9):pp. 618-624.

Kent et al., "Measurement of evoked potentials during thalamic deep brain stimulation", Brain Stimul, vol. 8, No. 1, Jan. 2015, p. 42-56.

(56)                    References Cited

OTHER PUBLICATIONS

Kilgore PhD et al., "Reversible Nerve Conduction Block Using Kilohertz Frequency Alternating Current," Neuromodulation. Aug. 2013, pp. 242-255.

Kumar et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Lo et al., "A Fully Integrated Wireless SoC for Motor Function Recovery after Spinal Cord Injury", IEEE Transactions on Biomedical Circuits and Systems, vol. 11, No. 3, Jun. 2017, pp. 497-509.

Lo et al., "Bio-Impedance Characterization Technique with Implantable Neural Stimulator Using Biphasic Current Stimulus", 36th Annual International Conference of the IEEE Engineering in Medicine and Biology Society, 2014, pp. 474-477, (Applicant points out, in accordance with MPEP 609.04(a), that the year of publication, 2014, is sufficiently earlier than the effective U.S. filing date, so that the particular month of publication is not an issue.).

Maeda et al., "Increased c-fos immunoreactivity in the spinal cord and brain following spinal cord stimulation is frequency-dependent," Brain Res. Mar. 9, 2009;1259: pp. 40-50, available online Jan. 6, 2009.

Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.

Maggi et al., "Effect of urethane anesthesia on the micturition reflex in capsaicin-treated rats." Journal of the Autonomic Nervous System, Jan. 1990, 30(3): 247-251.

North MD et al., "Clinical outcomes of 1 kHz subperception spinal cord stimulation (SCS): Results of a prospective randomized controlled crossover trial," Abstracts, International Neuromodulation Society, Jun. 2015, 1 pp.

North MD et al., "Spinal cord stimulation versus repeated lumbosacral spine surgery for chronic pain: a randomized, controlled trial," Neurosurgery, Jan. 2005; 56(1): 98-106; discussion 106-107.

Ranck Jr. et al., "Which elements are excited in electrical stimulation of mammalian central nervous system: a review," Brain Research, Nov. 21, 1975; 98(3): pp. 417-440.

Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato et al., "Spinal cord stimulation reduces hypersensitivity through activation of opioid receptors in a frequency-dependent manner," Eur J Pain. Apr. 2013 (4): pp. 551-561, first published Oct. 5, 2012.

Schu MD, PhD. et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.

Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.

Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.

Smith et al., "Successful use of high-frequency spinal cord stimulation following traditional treatment failure," Stereotact Funct Neurosurg. Apr. 1, 2015; 93(3): pp. 190-193.

Snellings et al., "Effects of stimulation site and stimulation parameters on bladder inhibition by electrical nerve stimulation," BJU International, Jul. 2012, pp. 136-143, first published Jan. 19, 2012.

Song MD Phd et al., "Efficacy of kilohertz-frequency and conventional spinal cord stimulation in rat models of different pain conditions," Neuromodulation Jan. 2014; 17(3): pp. 226-234.

Sweet MD et al., "High Frequency vs. Burst Stimulation Patterns for Dorsal Column Stimulation: The Importance of Charge," American Association of Neurological Surgeons, Abstract, Apr. 4, 2014, 2 pp.

Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.

Walter et al., "Inhibiting the hyperreflexic bladder with electrical stimulation in a spinal animal model." Neurourology and Urodynamics, 1993, 12:241-253. doi: 10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.

Wille MD et al., "Altering Conventional to High Density Spinal Cord Stimulation: An Energy Dose-Response Relationship in Neuropathic Pain Therapy," Neuromodulation 2016, Aug. 2016, 9 pp.

Woock et al., "Activation and inhibition of the micturition reflex by penile afferents in the cat," Am J. Physiol Regul Intergre Comp Physiol, published Apr. 23, 2008, pp. R1880-R1889.

Youn et al., The Effect of High-Frequency Stimulation on Sensory Thresholds in Chronic Pain Patients, Stereotact Funct Neurosurg, Oct. 8, 2015, pp. 355-359.

* cited by examiner

FIG. 1

SEATED ANTIDRONMIC BACK ARCH

MEASURED
STIMULATION
ARTIFACT
626

MEASURED
ECAP
628

NORMALIZED
METRIC
629

— STIM
...... ECAP

627

TIME (sec)

ECAP
NOT
AVAILABLE
630

SEATED CHAIR COUGH

First stimulation pulse
801

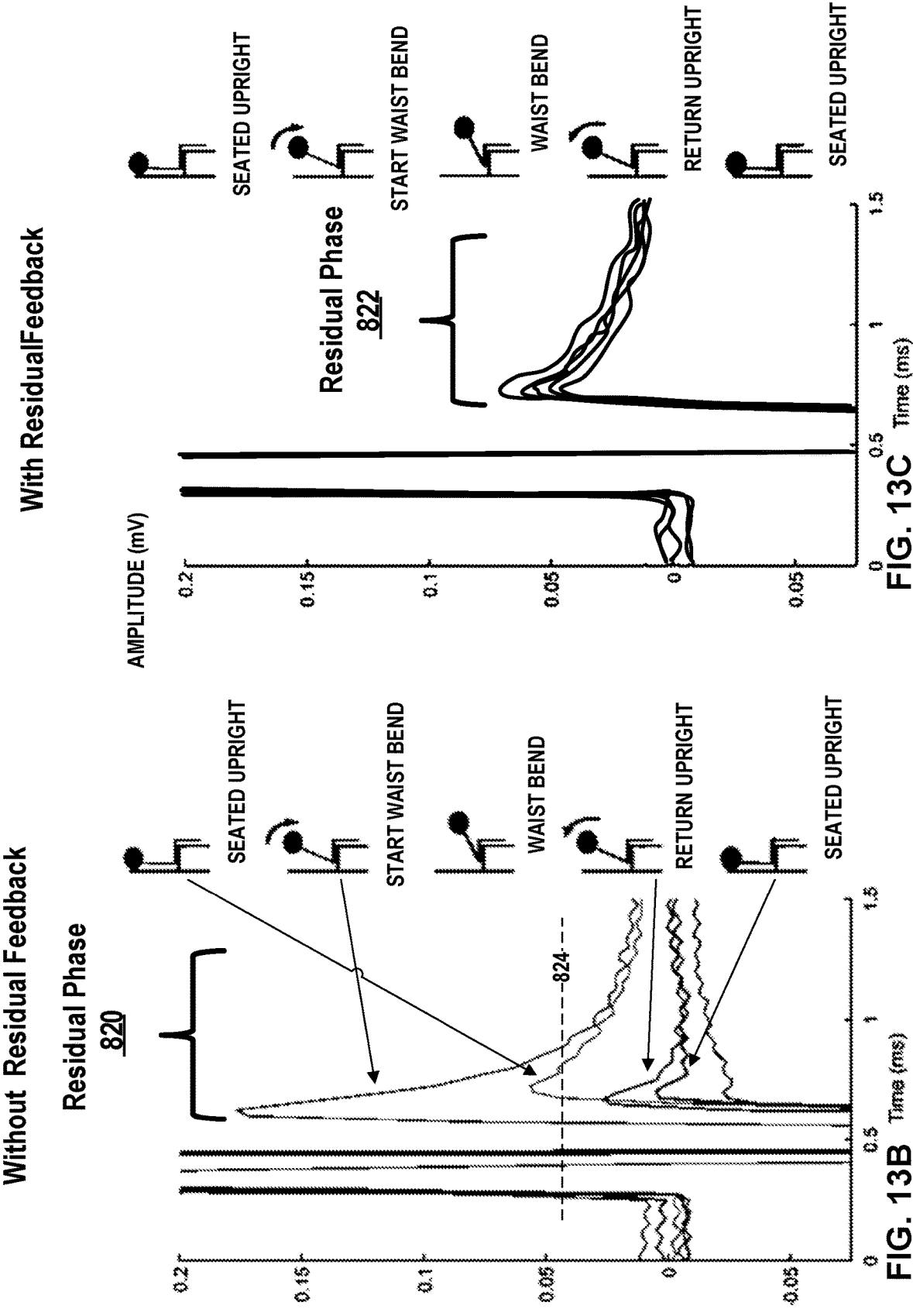

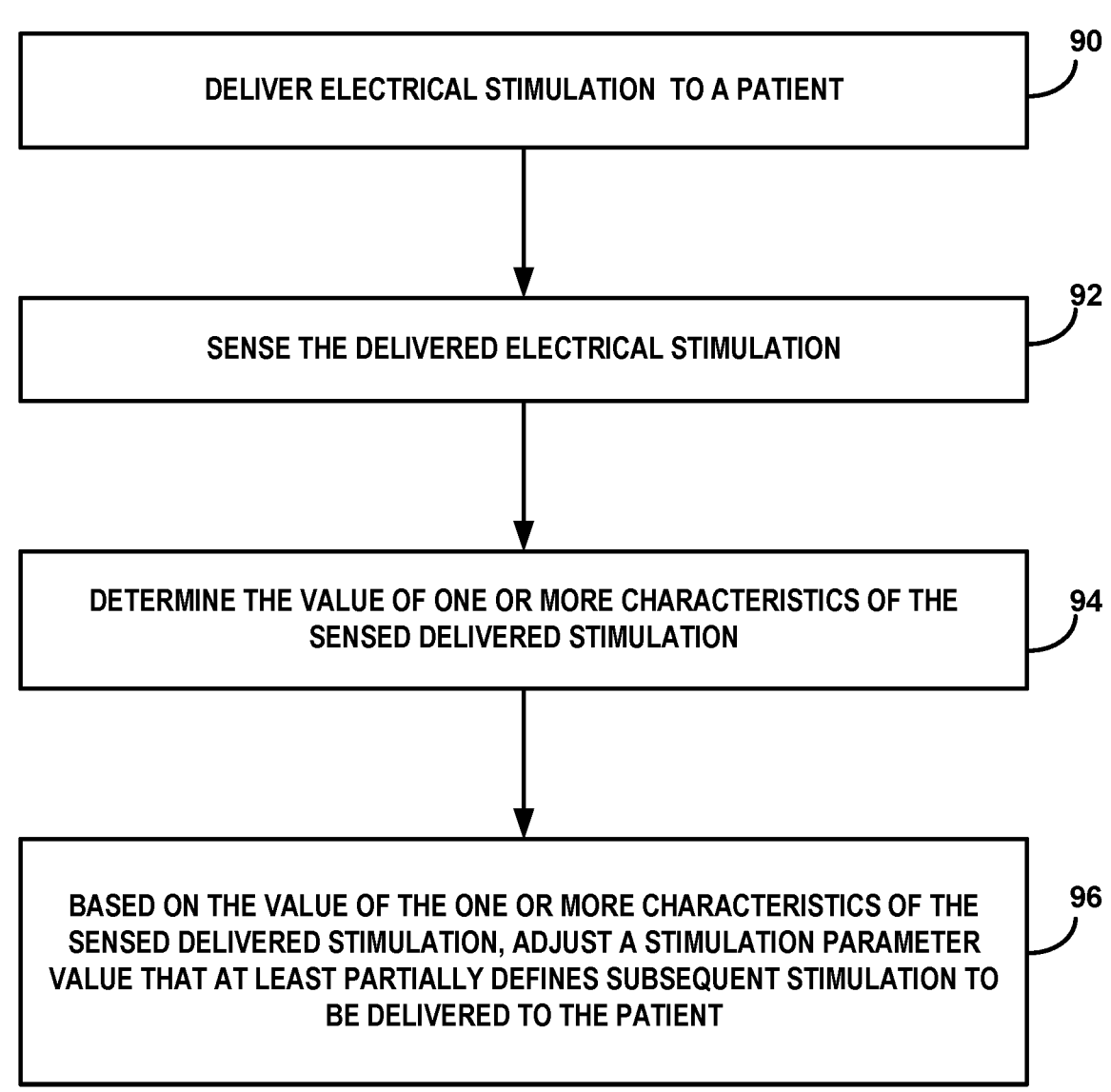

DELIVER ELECTRICAL STIMULATION TO A PATIENT
90

SENSE THE DELIVERED ELECTRICAL STIMULATION
92

DETERMINE THE VALUE OF ONE OR MORE CHARACTERISTICS OF THE SENSED DELIVERED STIMULATION
94

BASED ON THE VALUE OF THE ONE OR MORE CHARACTERISTICS OF THE SENSED DELIVERED STIMULATION, ADJUST A STIMULATION PARAMETER VALUE THAT AT LEAST PARTIALLY DEFINES SUBSEQUENT STIMULATION TO BE DELIVERED TO THE PATIENT
96

FIG. 14

FEEDBACK CONTROL OF ELECTRICAL STIMULATION THERAPY BASED ON ELECTRIC FIELD IMAGING

This application is a U.S. National Stage entry under 35 U.S.C. § 371 of International Application No. PCT/US2022/070796, filed Feb. 23, 2022 which claims priority from and the benefit of U.S. Provisional Patent Application No. 63/153,092, filed Feb. 24, 2021, the entire contents of each of which is incorporated herein by reference.

TECHNICAL FIELD

The disclosure relates sensing physiological parameters, and more specifically, analysis of a sensed signal indicative of a physiological parameter.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, the disclosure describes devices, systems, and techniques that use electric field imaging (often referred to as the sensed stimulation artifact representative of a delivered stimulus) as an informative feedback signal to provide closed loop control of electrical stimulation therapy. In some examples, the electric field imaging may be used in combination with other feedback signals, such as an ECAP signal, to monitor and adjust the delivered electrical stimulation therapy.

In one example, this disclosure describes a medical device that includes stimulation generation circuitry configured to deliver electrical stimulation to a patient; sensing circuitry configured to sense the delivered electrical stimulation; and processing circuitry operatively coupled to a memory, the processing circuitry configured to: determine the value of one or more characteristics of the sensed delivered stimulation; and based on the value of the one or more characteristics of the sensed delivered stimulation, adjust a stimulation parameter value that at least partially defines subsequent stimulation to be delivered to the patient.

In another example, this disclosure describes a medical device that includes stimulation generation circuitry configured to deliver a first stimulation pulse to a patient; sensing circuitry configured to sense a residual phase of the first stimulation pulse; and processing circuitry configured to: determine that a value of a characteristic of the sensed residual phase of the first stimulation pulse exceeds a target residual phase value; and responsive to determining that the value of the characteristic of the sensed residual phase exceeds the target residual phase value, change a first value of a parameter to a second value of the parameter that at least partially defines a second stimulation pulse deliverable by the stimulation generation circuitry after the residual phase of the first stimulation pulse was sensed.

BRIEF DESCRIPTION OF DRAWINGS

FIG. 1 is a conceptual diagram illustrating an example system that includes an implantable medical device (IMD) configured to deliver spinal cord stimulation (SCS) therapy and an external programmer, in accordance with one or more techniques of this disclosure.

FIGS. 13A, 13B and 13C are time graphs illustrating a stimulation pulse and the impact of sensed residual phase feedback.

FIG. 14 is a flow diagram illustrating an example operation of the system of this disclosure.

DETAILED DESCRIPTION

Figure 2:
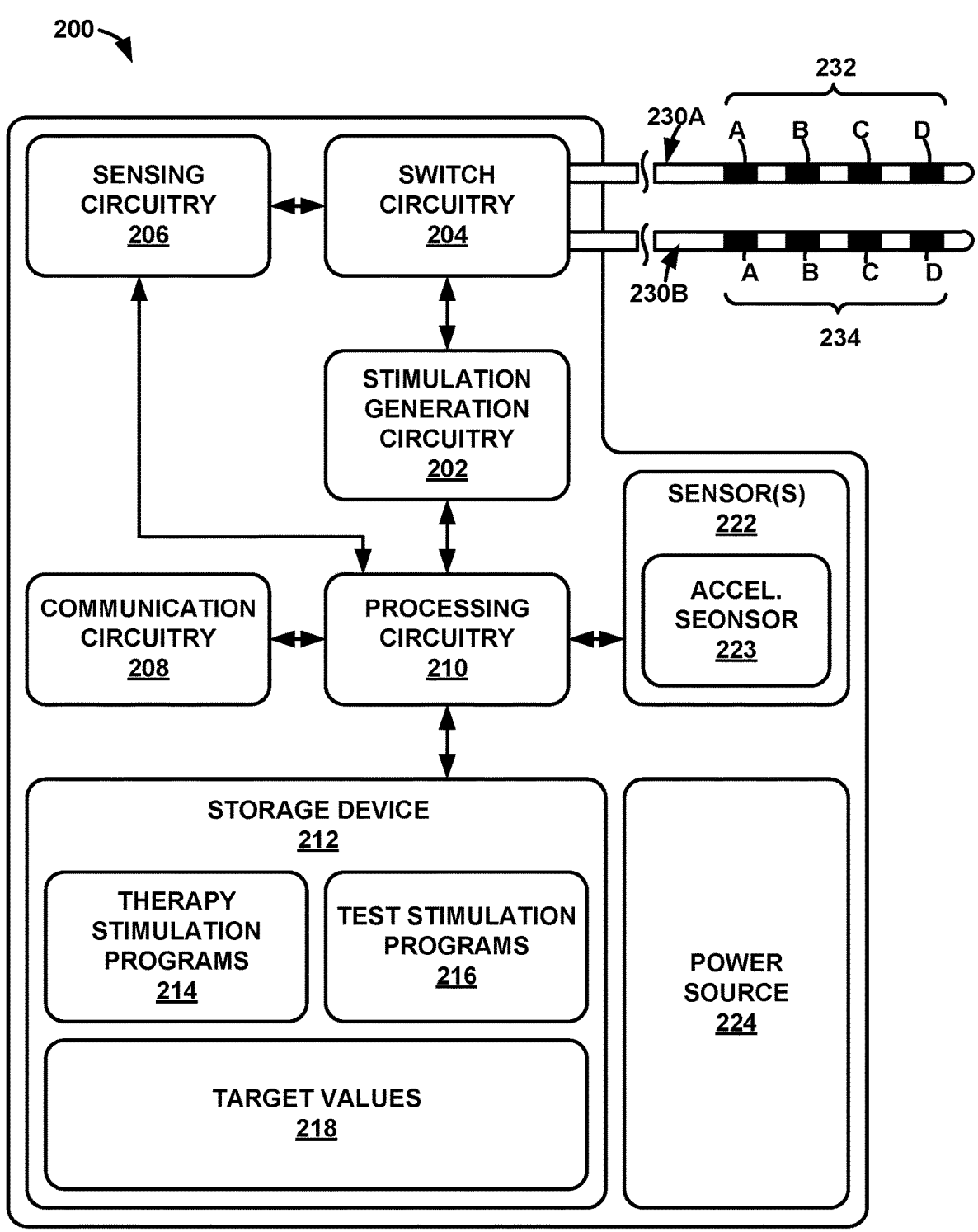
FIG. 2 is a block diagram illustrating an example configuration of components of the IMD of FIG. 1, in accordance with one or more techniques of this disclosure.

Techniques to use electric field imaging, which may be referred to as the stimulation artifact representing the sensed delivered electrical stimulus, as an informative feedback signal to provide closed loop monitoring and control of electrical stimulation therapy. In some examples, the electric field imaging may be used in combination with other feedback signals, such as ECAP, to monitor and adjust the delivered electrical stimulation therapy. Evoked neural activity (e.g., ECAPs) for feedback control may not always be observable in all patients. In some examples, sense electrodes may move too far from neural tissue receiving the electrical stimulation, e.g., based on certain patient activity and postures. In some examples, providing stimulation with a high enough magnitude to generate an ECAP may be undesirable for some patients because the stimulation intensity high enough to elicit a detectable ECAP signal may result in an uncomfortable sensation for some patients. Therefore, for some patients, sub-perception therapy may be preferred over stimulation that can be perceived (e.g., paresthesia). In this situations, the sub-threshold stimulation intensity may prevent the system from using the ECAP as a feedback signal in closed-loop stimulation because the sub-perception threshold stimulation may not elicit detectable ECAP signals.

As described herein, the system may control electrical stimulation delivery based, at least in part, on electric field imaging. In some examples, this electric field imaging may include sensing the electrical stimulation delivered to tissue (either stimulation intended to provide a therapeutic benefit to the patient or stimulation intended to be used for the electric field imaging which may or may not contribute to any therapeutic benefit). In some examples, electric field imaging may have some appealing features including: a strong, robust signal on all sense channels, changes in electric field imaging may track lead and/or body movement, and electric field imaging may be available for all non-zero sub-sensory threshold stimulation amplitudes. Furthermore, electric field imaging may be used with other feedback signals to provide more information about the patient state, which may improve existing control algorithms. Other feedback signals include but are not limited to: accelerometer signals indicating movement, posture, and activity, ECAP, biological impedance, temperature, heart rate, respiratory rate, and so on. Electric field imaging may be applicable to SCS therapy, as well applicable to other leaded neurostimulation products with multiple electrode contacts in movable regions, such as spinal cord stimulation (SCS), sacral neuromodulation (SNM), deep brain stimulation (DBS), and peripheral nerve stimulation (PNS), including tibial nerve stimulation, and so on. Electrical field imaging may also be described in this disclosure as sensing the electrical field from the delivered electrical stimulus.

Figure 1:
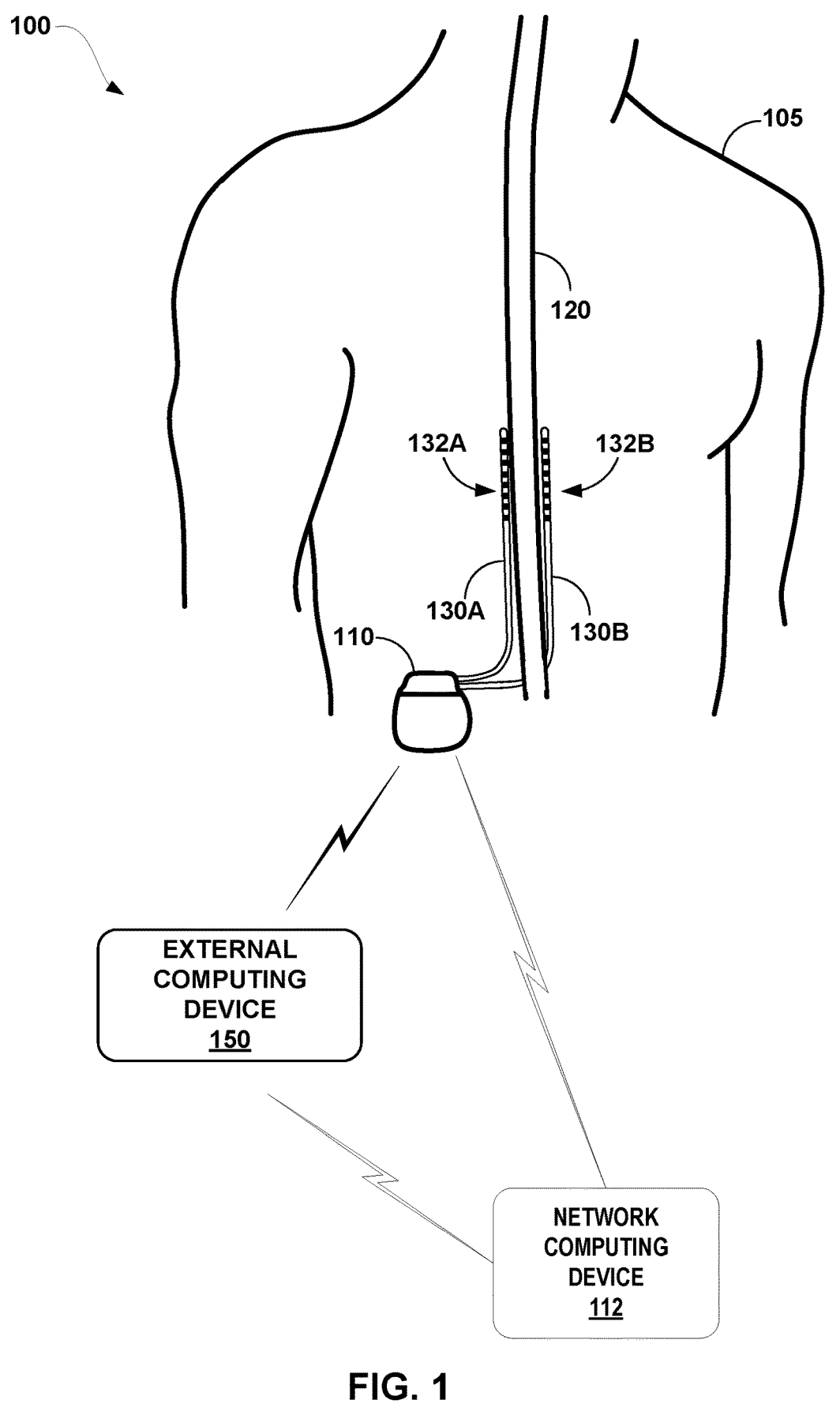

FIG. 1 is a conceptual diagram illustrating an example system 100 that includes an implantable medical device (IMD) 110 configured to deliver spinal cord stimulation (SCS) therapy and an external computing device 150, in accordance with one or more techniques of this disclosure. External computing device 150 may also be described as programmer 150 or external computing device 150.

Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices. In some examples, IMD 110 may be referred to as implantable neurostimulator (INS) 110.

IMD 110 and/or external computing device 150 may also communicate with network computing device 112. For example, processing circuitry of IMD 110 and external computing device 150 may, when requested, transmit any stored data in memory for review or further processing to network computing device 112. Network computing device 312 act as a server, such as a cloud based server, or a household server. In some examples network computing device 112 may be a tablet computer, laptop computer, desktop computer, mobile phone and so on. Network computing device 112 may include a user interface which may display outputs and accept inputs.

As shown in FIG. 1, system 100 includes an IMD 110, leads 130A and 130B, and external computing device 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively. "leads 130"), e.g., for relief of chronic pain or other symptoms. In other examples, IMD 110 may be coupled to a single lead carrying multiple electrodes or more than two leads each carrying multiple electrodes.

This electrical stimulation may be delivered in the form of stimulation pulses. In some examples, IMD 110 may be configured to generate and deliver stimulation pulses to include control pulses configured to elicit ECAP signals and/or cause IMD 110 to sense the delivered stimulation signals. The control pulses may or may not contribute to therapy in some examples. In some examples, IMD 110 may, in addition to control pulses, deliver informed pulses that contribute to the therapy for the patient, but which do not elicit detectable ECAPs or cause IMD 110 to detect every phase of responsive stimulation signals. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example. IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a leads 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, leads 130 may include a lead extension or other segments that may aid in implantation or positioning of leads 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes 132A and 132B (collectively electrodes 132) of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy.

The deployment of electrodes 132 via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead. Ring electrodes arranged at different axial positions at the distal ends of lead 130 will be described for purposes of illustration.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of stimulation pulses (e.g., control pulses and/or informed pulses) are typically predetermined parameter values determined prior to delivery of the stimulation pulses (e.g., set according to a stimulation program).

However, in some examples, system 100 changes one or more parameter values automatically based on one or more factors or based on user input.

A test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each test stimulation program are configured to evoke a compound action potential from nerves. In some examples, the test stimulation program defines when the control pulses are to be delivered to the patient based on the frequency and/or pulse width of the informed pulses when informed pulse are also delivered. In some examples, the stimulation defined by each test stimulation program are not intended to provide or contribute to therapy for the patient. In other examples, the stimulation defined by each test stimulation program may contribute to therapy when the control pulses elicit one or both of detectable ECAP signals and detect responsive stimulation signals. In this manner, the test stimulation program may define stimulation parameters the same or similar to the stimulation parameters of therapy stimulation programs.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, leads 130 includes one or more sensors configured to allow IMD 110 to monitor one or more parameters of patient 105, such as patient activity, pressure, temperature, or other characteristics. The one or more sensors may be provided in addition to, or in place of, therapy delivery by leads 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In some examples where relevant phases of stimulation signals cannot be detected from the types of pulses intended to be delivered to provide therapy to the patient, control pulses and informed pulses may be delivered. For example, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control stimulation pulses via the same, at least some of the same, or different electrodes. Since control stimulation pulses are delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. In other examples, a control stimulation pulse may include a tri-phasic pulse or pulse having more than three phases. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. In some cases, the control pulses may elicit an ECAP signal from the tissue, and IMD 110 may sense the ECAP signal via two or more electrodes on leads 130. In some examples, control pulses might not elicit ECAPs that are detectible by IMD 110, however IMD 110 may detect stimulation signals responsive to the control pulses. The control pulses may include information that is useful for determining parameters of one or more stimulation delivered to patient 105. In cases where the control stimulation pulses are applied to spinal cord 120, the signal may be sensed by IMD 110 from spinal cord 120.

IMD 110 may deliver control stimulation to a target stimulation site within patient 105 via the electrodes of leads 130 according to one or more test stimulation programs. The one or more test stimulation programs may be stored in a storage device of IMD 110. Each test program of the one or more test stimulation programs includes values for one or more parameters that define an aspect of the control stimulation delivered by IMD 110 according to that program, such as current or voltage amplitude, pulse width, pulse frequency, electrode combination, and, in some examples, timing based on informed pulses to be delivered to patient 105. In some examples, IMD 110 delivers control stimulation to patient 105 according to multiple test stimulation programs.

A user, such as a clinician or patient 105, may interact with a user interface of an external computing device 150 to program IMD 110. Programming of IMD 110 may refer generally to the generation and transfer of commands, programs, or other information to control the operation of IMD 110. In this manner, IMD 110 may receive the transferred commands and programs from external computing device 150 to control electrical stimulation therapy (e.g., informed pulses) and control stimulation (e.g., control pulses). For example, external computing device 150 may transmit therapy stimulation programs, test stimulation programs, stimulation parameter adjustments, therapy stimulation program selections, test program selections, user input, or other information to control the operation of IMD 110, e.g., by wireless telemetry or wired connection. As described herein, stimulation delivered to the patient may include control pulses, and, in some examples, stimulation may include control pulses and informed pulses.

In some cases, external computing device 150 may be characterized as a physician or clinician programmer if it is primarily intended for use by a physician or clinician. In other cases, external computing device 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external computing device 150 may include, or be part of, an external charging device that recharges a power source of IMD 110. In this manner, a user may program and charge IMD 110 using one device, or multiple devices. In some examples, external computing device 150 may also be referred to as recharger 150.

As described herein, information may be transmitted between external computing device 150 and IMD 110. Therefore, IMD 110 and external computing device 150 may communicate via wireless communication using any techniques known in the art. Examples of communication techniques may include, for example, radiofrequency (RF) telemetry and inductive coupling, but other techniques are also contemplated. In some examples, external computing device 150 includes a communication head that may be placed proximate to the patient's body near the IMD 110 implant site to improve the quality or security of communication between IMD 110 and external computing device 150. Communication between external computing device 150 and IMD 110 may occur during power transmission or separate from power transmission.

In some examples, IMD 110, in response to commands from external computing device 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

Efficacy of electrical stimulation therapy may, in some cases, be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Additionally, or alternatively, efficacy of electrical stimulation therapy may be indicated by one or more characteristics (e.g., a voltage magnitude) of a stimulation signal that is sensed in response to the stimulation pulse delivered by IMD 110. The stimulation signal may be indicative of the detection of the delivered stimulation pulse and related signals instead of action potentials evoked by the delivered stimulation pulse. In this disclosure, sensing the delivered stimulation signal may also be referred to as a stimulation artifact, or as electrical field imaging.

In one or more cases where stimulation pulses elicit detectible ECAPs, electrical stimulation therapy delivery by leads 130 of IMD 110 may cause neurons within the target tissue to evoke a compound action potential that travels up and down the target tissue (e.g., nerve fibers), eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one or more cases where a stimulation pulse causes IMD 110 to sense one or more respective stimulation signals, one or more characteristics of the respective stimulation signal may indicate an efficacy of the electrical stimulation delivered to patient 105 by IMD 110. For example, it may be beneficial for a voltage magnitude of the stimulation signal to be at a target stimulation signal value. In one example, the target stimulation signal value may be a target range from a first threshold magnitude value to a second threshold magnitude value. If the voltage magnitude of the stimulation signal is less than the first threshold magnitude value, the electrical stimulation might not be as effective at treating pain perceived by patient 105 as compared with scenarios in which the voltage magnitude of the stimulation signal is within the target range. On the other hand, if the voltage magnitude of the stimulation signal is greater than the second threshold magnitude value, the electrical stimulation might be inducing an uncomfortable (e.g., unwanted or painful) sensation perceived by patient 105 as compared with examples in which the voltage magnitude of the stimulation signal is within the target range. In some examples, IMD 110 may control the voltage magnitude of the stimulation signal to be within a target range by changing and/or setting one or more parameters of subsequent stimulation pulses (e.g., control pulses and/or informed pulses) delivered to patient 105 in response to measuring the voltage magnitude of one or more detected stimulation signals.

Additionally. or alternatively, the target stimulation signal value (e.g., the target range) of characteristic values of the stimulation signals may depend on a posture of patient 105. For example, IMD 110 may include an accelerometer (not illustrated in FIG. 1) which is configured to generate an accelerometer signal. IMD 110 may be configured to determine, based on the accelerometer signal, a posture of patient 105. The determined posture may be a posture of a set of postures including a standing posture, a seated posture, a supine posture, a prone posture, and a side-lying posture, as examples, IMD 110 may be configured to select the target range of characteristic values of a stimulation signal based on the determined posture of patient 105. As discussed above, in some examples, the IMD 110 may be configured to select the target stimulation signal value of the stimulation signal based on a magnitude of the stimulation pulse which causes IMD 110 to sense the stimulation signal in addition to selecting the target range of characteristic values based on the posture of patient 105. In fact, the target range of characteristic values for a particular stimulation signal may be defined by one or more "transfer functions," where each posture of the set of postures being associated with a respective transfer function.

In the example of FIG. 1, IMD 110 is described as performing a plurality of processing and computing functions. However, external computing device 150 instead may perform one, several, or all of these functions. In this alternative example, IMD 110 functions to relay sensed signals to external computing device 150 for analysis, and external computing device 150 transmits instructions to IMD 110 to adjust the one or more parameters defining the electrical stimulation therapy based on analysis of the sensed signals. For example, IMD 110 may relay the sensed signal indicative of a stimulation signal to external computing device 150. External computing device 150 may compare a characteristic value of the stimulation signal to the respective target range of characteristic values, and in response to the comparison, external computing device 150 may instruct IMD 110 to adjust one or more parameters that define the electrical stimulation pulses delivered to patient 105.

In some examples, stimulation generation circuitry of IMD 110 may be configured to deliver at least one stimulation pulse between a time in which the stimulation generation circuitry delivers a first stimulation pulse and a time in which the stimulation generation circuitry delivers a second stimulation pulse which is based on a stimulation signal responsive to the first stimulation pulse. In some examples, stimulation generation circuitry of IMD 110 may be configured to deliver the second stimulation pulse consecutive to the first stimulation pulse.

The feasibility of stimulation artifact as a feedback signal is based on data from open loop (OL) and closed loop (CL)

studies. General steps may include: quantify stimulation artifact; examine correlation to ECAP signal; examine change in artifact during CL ECAP control; construct prototype artifact control algorithm; simulate artifact control algorithm (e.g., determine how stimulation amplitude in CL ECAP datasets evolve as control algorithm predicts); prototype in humans. Whole lead recordings from spinal leads data gathered during prototyping of ECAPS has been analyzed to see that the electric field (stimulation artifact) changes with stimulus amplitude, patient movement aggressors, and is correlated to ECAP amplitude as well. Thus, the electric field image (stimulation artifact) makes a good candidate for feedback control.

A neural response following an ECAP stimulation pulse may not be observed in all patients. ECAPs may not be recorded to high-rate burst stimulation, and certainly not at subthreshold levels may help provide optimal dosing to the cord (without overstimulation) and help address habituation and loss of therapy In some examples, based on large movement of the patient, the stim-to-artifact response may change significantly. Processing circuitry may calibrate expected stim artifact to stim output.

Sub-perception threshold electrical stimulation that effectively relieves symptoms of patient 105 may still have high enough intensity (magnitude, pulse width and so on) that may saturate sensing circuitry. In some examples, medical devices may disable or "blank" sensing circuitry while delivering the stimulation to avoid saturating sensitive circuitry, e.g., implement a blanking window to block sensing.

Some example implementation techniques to use electric field images (stimulation artifact) as feedback signal may include:

Interleaved, low stimulation dosage monitor "ping" pulses to avoid saturation of recording electronics, where stimulation dosage and stimulation intensity may refer to the strength of the delivered electrical stimulation, e.g., amplitude, pulse width, and so on;

Dedicated low gain recording pathway for artifact signals to avoid saturation of recording electronics;

Strategic choice of recording electrodes relative to stimulation electrodes on the same lead to increase/decrease the sensitivity of the electric field imaging to lead/body movement:

Proximity of the spinal lead to tissue is reflected in the pattern of spread of electric fields generated electrodes. In some examples, sensing circuitry may measure the spread with single recording electrode, while stimulating all the other contacts. In other examples, measure higher-dimensional pattern of spread using all combinations of recording and stimulating contacts, which may be useful to track relative lead movement.

Figure 7:
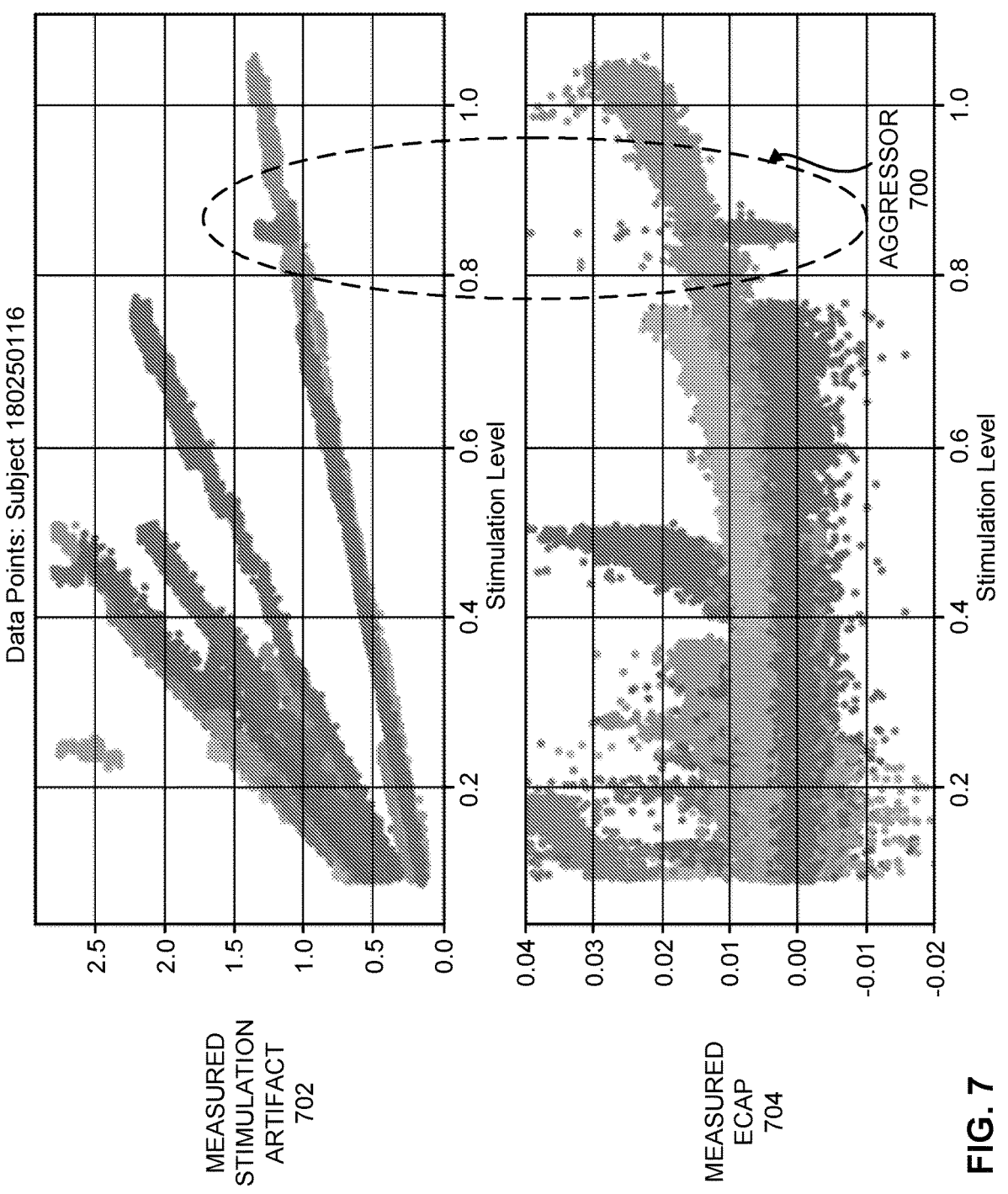
FIG. 7 is a graph illustrating growth curves for the stimulation artifact and measured ECAP with an aggressor.
Figure 12A:
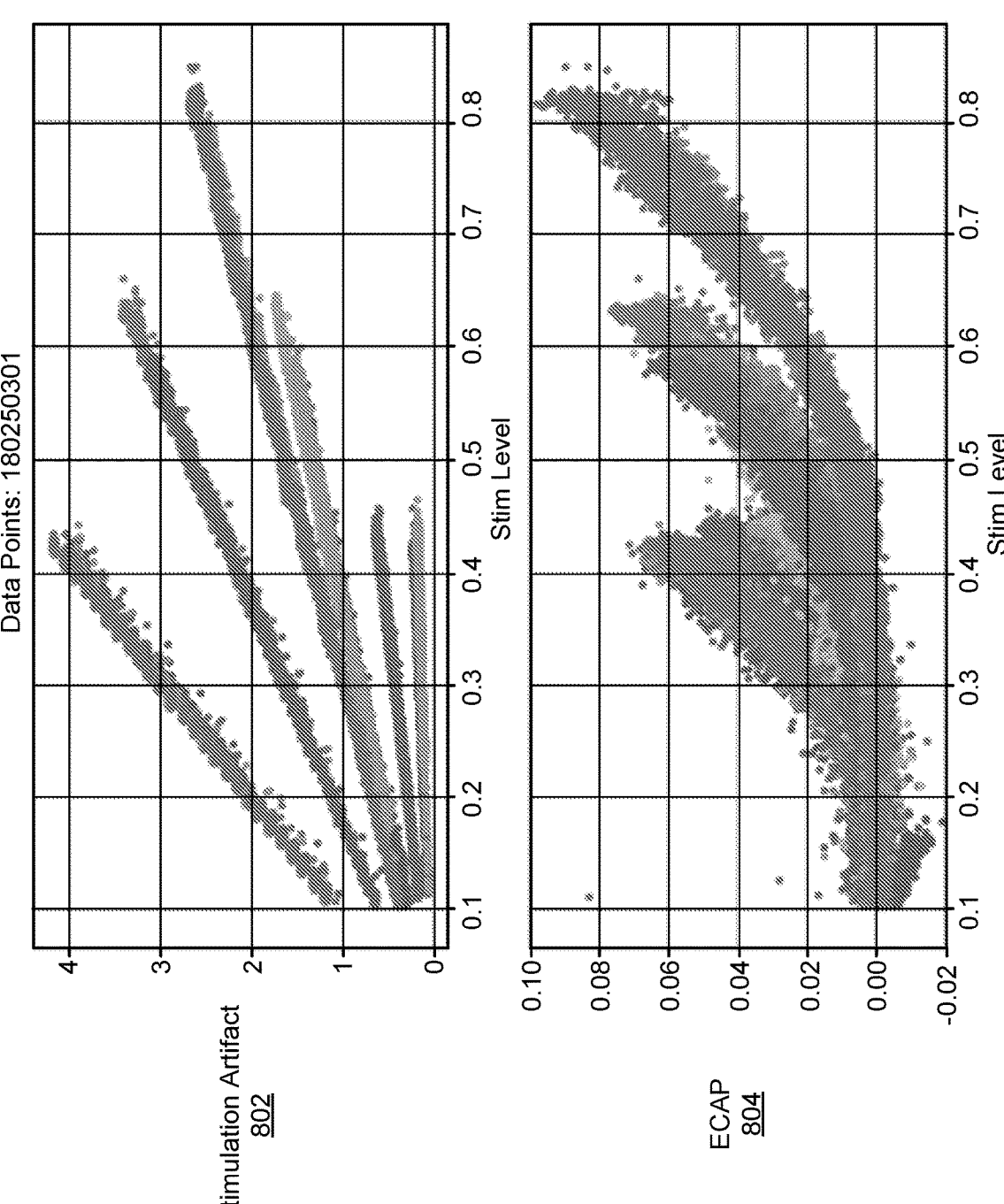
FIGS. 12A, 12B and 12C are graphs illustrating growth curves of the stimulation artifact and measured ECAP.

The processing circuitry may receive sensed electric field imaging as the feedback control signal. In some examples the processing circuitry may:

Automatically adjust stimulation amplitude of the informed pulses up/down based on change of the electric field from the "nominal" desired level;

Use electric field growth curves (analogous to ECAP growth curves) that are positively sloped linear curves across the entire range of stimulation amplitude and thus provide feedback across the entire range of amplitude, e.g., measured stimulation artifact signals may not drop out at the low end of the stimulation as ECAP growth curves do when a delivered stimulation no longer elicits an ECAP signal, as shown in FIGS. 7 and 12A.

Processing circuitry may use a combination of electric field imaging with other signals for feedback control, for example:

Use change in accelerometer signal to trigger either/both sensing of ECAP and electric field signals to save battery life:

Use change in electric field to trigger sensing of ECAPs may save battery life and ensure stimulation stays sub-perception. For example, if the stimulation artifact (electric field) is too high or too low, then processing circuitry may monitor for ECAP;

A relationship between the electric field and "zingers" dependent on the individual. Can utilize ECAP to establish individual's correlation between electric field changes and zingers; afterwards can stop using ECAPS (or only use to re-check mapping). In this disclosure a "zinger" may be a stimulation therapy pulse of undesired intensity that feels like "shock" for the patient, for example when the electrodes move closer to the spinal cord during movement. Such a therapy pulse may also be called "transient events" because they only happen for short periods of time, e.g., an acute duration, and come quickly (like due to a cough, sneeze, laugh, etc.).

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, communication circuitry 208, processing circuitry 210, storage device 212, sensor(s) 222, and power source 224. As seen in FIG. 2, sensor(s) 222 include acceleration sensor 223.

In the example shown in FIG. 2, storage device 212 stores therapy stimulation programs 214 and test stimulation programs 216 in separate memories within storage device 212 or separate areas within storage device 212. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored test stimulation programs 216 defines values for a set of electrical stimulation parameters (e.g., a control stimulation parameter set), such as a stimulation electrode combination, electrode polarity, current or voltage amplitude, pulse width, pulse rate, and pulse shape. Test stimulation programs 216 may also have additional information such as instructions regarding when to deliver control pulses based on the pulse width and/or frequency of the informed pulses defined in therapy stimulation programs 214. In examples in which control pulses are provided to the patient without the need for informed pulses, a separate test stimulation program may not be needed. Instead, the test stimulation program for therapy that only includes control pulses may define the same control pulses as the corresponding therapy stimulation program for those control pulses.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs, biological impedance, electrical field imaging and so on. Additionally, or alternatively, sensing circuitry 206 may sense one or more stimulation pulses delivered to patient 105 via electrodes 232, 234. In some examples, sensing circuitry 206 detects electrical signals, such as stimulation signals and/or ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Communication circuitry 208 supports wireless communication between IMD 200 and an external computing device (not shown in FIG. 2) or another computing device under the control of processing circuitry 210. Processing circuitry 210 of IMD 200 may receive, as updates to programs, values for various stimulation parameters such as amplitude and electrode combination, from the external computing device via communication circuitry 208. Updates to the therapy stimulation programs 214 and test stimulation programs 216 may be stored within storage device 212. Communication circuitry 208 in IMD 200, as well as communication circuits in other devices and systems described herein, such as the external programmer, may accomplish communication by radiofrequency (RF) communication techniques. In addition, communication circuitry 208 may communicate with the external medical device programmer (not shown in FIG. 2) via proximal inductive interaction of IMD 200 with the external programmer. The external computing device may be one example of external computing device 150 and network computing device 112 of FIG. 1. Accordingly, communication circuitry 208 may send information to the external computing device on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. Electrodes 232 are examples of electrodes 132 described above in relation to FIG. 1. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques.

In some examples, one or more of electrodes 232 and 234 are suitable for sensing one or more ECAPs. For instance, electrodes 232 and 234 may sense the voltage amplitude of a portion of the ECAP signals, where the sensed voltage amplitude is a characteristic of the ECAP signal.

In some examples, one or more of electrodes 232 and 234 are suitable for electric field imaging, e.g., for sensing delivered stimulation signals. For instance, electrodes 232 and 234 may sense the voltage amplitude of a portion of the stimulation signals, where the sensed voltage amplitude is a characteristic of the stimulation signals. In some examples, one or more of electrodes 232 and 234 may sense a stimulation signal in response to one or more of electrodes 232 and 234 delivering a stimulation pulse to target tissue of patient 105. In some examples, the one or more of electrodes 232 and 234 which sense the stimulation signal are not the same as the one or more of electrodes 232 and 234 which deliver the stimulation pulse.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214, test stimulation programs 216, and target values 218.

In some examples, stimulation generation circuitry 202 may be configured to deliver electrical stimulation therapy to patient 105. In some examples, the electrical stimulation therapy may include a plurality of informed pulses. Additionally, stimulation generation circuitry 202 may be configured to deliver a plurality of control pulses, where the plurality of control pulses is interleaved with at least some informed pulses of the plurality of informed pulses. Stimulation generation circuitry may deliver the plurality of informed pulses and the plurality of control pulses to target tissue (e.g., spinal cord 120) of patient 105 via electrodes 232, 234 of leads 230. By delivering such informed pulses and control pulses, stimulation generation circuitry 202 may cause IMD 200 to sense stimulation signals that are indicative of the delivered pulses Additionally, or alternatively, stimulation generation circuitry 202 may deliver control pulses that evoke detectable responsive ECAPs in the target tissue, the responsive ECAPs propagating through the target tissue before arriving back at electrodes 232, 234. Stimulation signals or ECAPs caused by or elicited by informed pulses may not be detectable by IMD 200. In some examples, a different combination of electrodes 232, 234 may be configured to sense responsive ECAPs and/or responsive stimulation signals than the combination of electrodes 232, 234 used to deliver the informed pulses and the combination of electrodes 232, 234 used to deliver control pulses. Sensing circuitry 206 may be configured to detect the responsive ECAPs and/or the electric field imaging via electrodes 232, 234 and leads 230. In other examples, stimulation generation circuitry 202 may be configured to deliver a plurality of control pulses, without any informed pulses, when control pulses also provide or contribute to a therapeutic effect for the patient.

Processing circuitry 210 may, in some cases, direct sensing circuitry 206 to continuously monitor for ECAPs and stimulation signals. In other cases, processing circuitry 210 may direct sensing circuitry 206 to monitor for ECAPs and electric field imaging based on signals from sensor(s) 222. For example, processing circuitry 210 may activate sensing circuitry 206 based on an activity level of patient 105 exceeding an activity level threshold (e.g., acceleration sensor 223 rises above a threshold). Activating and deactivating sensing circuitry 206 may, in some examples, extend a battery life of power source 224.

Processing circuitry 210 may determine whether electrical stimulation therapy delivered to target tissue of patient 105 via electrodes 232, 234 elicits enough detectible ECAPs for processing circuitry 210 to determine therapy based on one or more characteristics of the respective detectible ECAPs. It may be beneficial for processing circuitry 210 to determine therapy based on characteristics of detectible ECAPs rather than characteristics of detectible electric field imaging, if possible. However, if not enough responsive ECAPs are detectible by sensing circuitry 206, it may be beneficial for processing circuitry 210 to determine therapy based on one or more characteristics of respective electric field imaging, which are often still detectible even when some or all of elicited ECAPs are not detectible in response to a stimulation pulse. In addition, sensing circuitry 206 may still detect delivered electrical stimulation signals when the delivered stimulation pulses were insufficient to elicit a detectable ECAP signal (e.g., when the delivered stimulation pulses are configured to be sub-threshold pulses). Examples of sensed characteristics for electric field imaging may include a magnitude of a current pulse, pulse width, timing between delivery and sensed pulse, one or more ratios, frequency, and other characteristics.

In one example, to determine if the electrical stimulation therapy elicits enough detectible ECAPs, processing circuitry 210 is configured to perform a test to determine whether the plurality of pulses of the electrical stimulation therapy elicit greater than a threshold ratio of detectible ECAPs. For example, to perform the test, processing circuitry 210 may identify a set of ECAPs elicited by a sequence of consecutive pulses of the plurality of pulses. Subsequently, processing circuitry 210 may calculate a ratio of the set of ECAPs to the sequence of consecutive pulses. For example, processing circuitry 210 may first determine a number of ECAPs of the set of ECAPs and a number of pulses of the sequence of consecutive pulses, and then calculate a ratio of the number of ECAPs to the number of pulses.

There may be cases in which a particular one or more stimulation pulses of the sequence of consecutive pulses might not elicit ECAPs that are detectible by sensing circuitry 206, but another one or more stimulation pulses of the sequence of consecutive pulses do elicit ECAPs that are detectible by sensing circuitry 206. In such cases, processing circuitry 210 may be configured to determine therapy based on one or more characteristics of the detectible ECAPs rather than determine therapy based on one or more characteristics of detectible stimulation signals. In some examples, processing circuitry 210 may determine whether the ratio of detectible ECAPs to stimulation pulses is greater than the threshold ratio. In one or more cases where the ratio is greater than the threshold ratio, processing circuitry 210 may determine therapy based on characteristics of the detectible ECAPs. In one or more cases where the ratio is not greater than the threshold ratio, processing circuitry 210 may determine therapy based on characteristics of the detectible stimulation signals.

In some examples, responsive to determining that a plurality of pulses elicit greater than a threshold ratio of detectible ECAPs, processing circuitry 210 is configured to set, based on one or more characteristics of an ECAP, one or more parameters which at least partially define the one or more pulses deliverable by stimulation generation circuitry

202 after a stimulation pulse which elicits the respective ECAP. In some examples, responsive to determining that a plurality of pulses do not elicit greater than a threshold ratio of detectible ECAPs, processing circuitry 210 is configured to set, based on one or more characteristics of a stimulation signal, one or more parameters which at least partially define the one or more pulses deliverable by stimulation generation circuitry 202 after a stimulation pulse which elicits the respective stimulation signal. In some examples, processing circuitry 210 may set one or more parameters which at least partially define the one or more pulses deliverable by stimulation generation circuitry 202 based on a combination of characteristics of one or more detectable ECAPs and characteristics of one or more detectible stimulation signals.

Stimulation generation circuitry 202 may be configured to deliver one or more stimulation pulses, at least one of which may cause sensing circuitry 206 to sense the delivered stimulation signal (electric field imaging) in response to the delivery of the respective pulse. In some examples, to sense a stimulation signal, sensing circuitry 206 may detect, via any one or combination of electrodes 232, 234, one or more electrical signals which are generated by stimulation generation circuitry 202 and delivered to patient 105 via any one or combination of electrodes 232, 234. In some examples, electric field imaging may include information which is useful for determining one or more parameters of subsequent therapy pulses generated by stimulation generation circuitry 202. For example, information gleaned from electric field imaging may include one or more characteristics of the sensed, delivered electrical stimulation signal, which indicate an efficacy of therapy delivered to patient 105 via electrodes 232, 234. In some cases, the one or more characteristics may reflect a separation between one or more of electrodes 232, 234 and target tissue of patient 105 (e.g., spinal cord 120). Such a distance between electrodes 232, 234 and spinal cord 120 may be relevant to determining therapy since a smaller intensity (e.g., amplitude and/or pulse length) of therapy pulses is required to stimulate a nerve if electrodes 232, 234 move closer to spinal cord 120 and vice versa.

Processing circuitry 210 may be configured to compare a characteristic value of a stimulation signal to a target stimulation signal value and adjust a stimulation parameter value based on the comparison. For example, processing circuitry may be configured to determine whether a characteristic value of a stimulation signal is within a range from a first threshold characteristic value to a second threshold characteristic value. As noted above, in some examples, the characteristic value may include an amplitude of the stimulation signal, an amplitude of a portion of the stimulation signal, timing, a slope of a portion of the stimulation signal, an area under a curve of at least a portion of the stimulation signal, or any combination thereof. In this way, sensing circuitry 206 may be configured to determine whether an amplitude of a portion of the stimulation signal is within a range from a first threshold amplitude value for the portion of the stimulation signal to a second threshold amplitude value for the portion of the stimulation signal, for example, but this is not required. The characteristic value may represent any measurable characteristic of a stimulation signal.

Responsive to determining that the characteristic value of the stimulation signal is not within a range from a first threshold characteristic value to a second threshold characteristic value, processing circuitry 210 may change one or more parameters which at least partially define one or more pulses deliverable by the stimulation generation circuitry after the stimulation signal as compared with the one or more parameters which at least partially define one or more pulses deliverable by the stimulation generation circuitry before the stimulation signal. In some examples, processing circuitry 210 may determine that the characteristic value is lower than the first threshold characteristic value.

In response to the characteristic value being lower than the first threshold characteristic value, processing circuitry 210 may be configured to increase (e.g., increment) one or more parameters which at least partially define one or more pulses deliverable by stimulation generation circuitry 202 after the stimulation signal (e.g., increase one or more parameters which define pulses of therapy stimulation programs 214 and/or test stimulation programs 216). In some examples, processing circuitry 210 may increase the one or more parameters proportional to an amount that the characteristic value is lower than the first threshold characteristic value. In some examples, processing circuitry 210 may increase the one or more parameters by a predetermined amount no matter the amount that the characteristic value is lower than the first threshold characteristic value. In some examples, processing circuitry 210 may increase the one or more parameters according to a function, where an input to the function is the characteristic value of the stimulation signal.

In response to the characteristic value being greater than the second threshold characteristic value, processing circuitry 210 may be configured to decrease (e.g., decrement) one or more parameters which at least partially define one or more pulses deliverable by stimulation generation circuitry 202 after the stimulation signal (e.g., decrease one or more parameters which define pulses of therapy stimulation programs 214 and/or test stimulation programs 216). In some examples, processing circuitry 210 may decrease the one or more parameters proportional to an amount that the characteristic value is greater than the second threshold characteristic value. In some examples, processing circuitry 210 may decrease the one or more parameters by a predetermined amount no matter the amount that the characteristic value is greater than the second threshold characteristic value. In some examples, processing circuitry 210 may decrease the one or more parameters according to a function, where an input to the function is the characteristic value of the stimulation signal.

Processing circuitry 210 may maintain one or more parameters of which at least partially define one or more pulses deliverable by stimulation generation circuitry 202 after a respective stimulation signal responsive to determining that a value of a characteristic of the stimulation signal is within a range from a first threshold characteristic value to a second threshold characteristic value. For example, if the characteristic of the stimulation signal is within the range, this may indicate that the one or more parameters which at least partially define one or more pulses deliverable by stimulation generation circuitry 202 are within a desired range.

A characteristic value of a stimulation signal may, in some cases, depend on one or more parameters of the delivered pulse (e.g., pulse amplitude, pulse duration, area under a curve of the pulse, pulse shape, pulse slope, or any combination thereof) from which sensing circuitry 206 detects one or more stimulation signal. For example, determining therapy based on a stimulation signal may, in some cases, depend on an amplitude of the pulse which causes sensing circuitry 206 to detect the stimulation signal. This is because sensing circuitry 206 senses stimulation signals by detecting electrical signals indicative of stimulation pulses delivered by electrodes 232, 234. In this way, it may be expected that a first stimulation pulse having a first amplitude will cause sensing circuitry 206 to detect a stimulation signal having an amplitude within a first range of amplitude values. Additionally, it may be expected that a second stimulation pulse having a second amplitude will cause sensing circuitry 206 to detect a stimulation signal having an amplitude within a second range of amplitude values. If the first amplitude of the first stimulation pulse is lower than the second amplitude of the second stimulation pulse, a lower-bound of the first range may be lower than a lower-bound of the second range and an upper-bound of the first range may be lower than an upper-bound of the second range. In some examples, a range of target amplitude values for a stimulation signal may be linearly related to an amplitude of a stimulation pulse which causes sensing circuitry 206 to detect the stimulation signal. Storage device 212 may store target values 218 which include a set of target ranges and other target values, where each target range and target value of target values 218 corresponds to a respective stimulation pulse amplitude value of a set of stimulation pulse amplitude values.

Determining therapy based on one or more electric field imaging may, in some examples, depend on a posture of patient 105. For example, processing circuitry 210 may be configured to determine a posture of patient 105 based on an acceleration signal generated by acceleration sensor 223. In some examples, the accelerometer signal includes a vertical component, a lateral component, and a frontal component corresponding to a vertical axis, a lateral axis, and a frontal axis, respectively. In this way, the accelerometer signal represents a three-dimensional measurement of acceleration. It may be beneficial for processing circuitry 210 to analyze one or more of the vertical axis, the lateral axis, and the frontal axis in order to determine a posture of patient 105.

In some examples, acceleration sensor 223 is configured to generate an accelerometer signal. Processing circuitry 210 is configured to identify, based on the accelerometer signal, a posture of a set of postures which patient 105 is occupying. The set of postures may include, for example, a standing posture, a sitting posture, a supine posture, a prone posture, a side-lying posture, or any combination thereof. In some examples, expected parameter values of the accelerometer signal corresponding to each posture of the set of postures are stored in storage device 212. Subsequently, processing circuitry 210 may select, based on the identified posture, a target stimulation signal value (e.g., a target range of characteristic values) for a stimulation signal sensed by IMD 200 in response to a delivery of a corresponding stimulation pulses. For example, if stimulation generation circuitry 202 generates a stimulation pulse having a stimulation amplitude and delivers the stimulation pulse to target tissue of patient 105 via one or a combination of electrodes 232, 234, processing circuitry 210 may select, based on a posture of patient 105 during the delivery of the stimulation pulse, a target range for a characteristic of the resulting stimulation signal sensed by sensing circuitry 106. Subsequently, processing circuitry 210 may determine whether to change one or more parameters of therapy stimulation programs 314 and/or test stimulation programs 216 based on whether the characteristic value is within the target range of characteristic values selected based on the posture of patient 105.

In some examples, processing circuitry 210 is configured to identify, based on the accelerometer signal, a posture of a set of postures which patient 105 is occupying while a stimulation pulse is delivered and identify an amplitude of the stimulation pulse. Subsequently, processing circuitry 210 may select a target range of characteristic values for a characteristic of a stimulation signal sensed by sensing circuitry 206 in response to the delivery of the stimulation pulse based on both of the posture of patient 105 and the amplitude of the stimulation pulse. For example, target values 218 may include a respective transfer function corresponding to each posture of the set of postures. Each transfer function represents a relationship (e.g., a linear relationship) between the amplitude of a stimulation pulse and the target stimulation signal value (e.g., a target range of characteristic values) for a stimulation signal sensed by IMD 200 in response to the delivery of the stimulation pulse. As such, processing circuitry 210 may, when evaluating whether to change one or more parameters of upcoming stimulation pulses, first select a transfer function corresponding to a present stimulation pulse and subsequently select a target range of characteristics based on the amplitude of the present stimulation pulse, but this is not required. Processing circuitry 210 may first analyze the amplitude of the stimulation pulse and subsequently determine the posture of patient 105, in some examples.

In some examples, processing circuitry 210 is configured to determine, based on the accelerometer signal generated by acceleration sensor 223, a transition from a first posture to a second posture of the set of postures. Responsive to determining the transition from the first posture to the second posture, processing circuitry 210 is configured to update the target stimulation signal value (e.g., the target range of characteristic values) for a respective sensed stimulation signal from a first target stimulation signal value to a second target stimulation signal value. In some examples, the detected change in posture may trigger the transition from a first target range to a second target range, but this is not required. In some cases, processing circuitry 102 may monitor the posture of patient 105 and the amplitude of stimulation pulses generated by stimulation generation circuitry 202 in real time or near real-time. Accordingly, processing circuitry 210 may set the range of target characteristic values for responsive stimulation signals in real time or near real-time.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
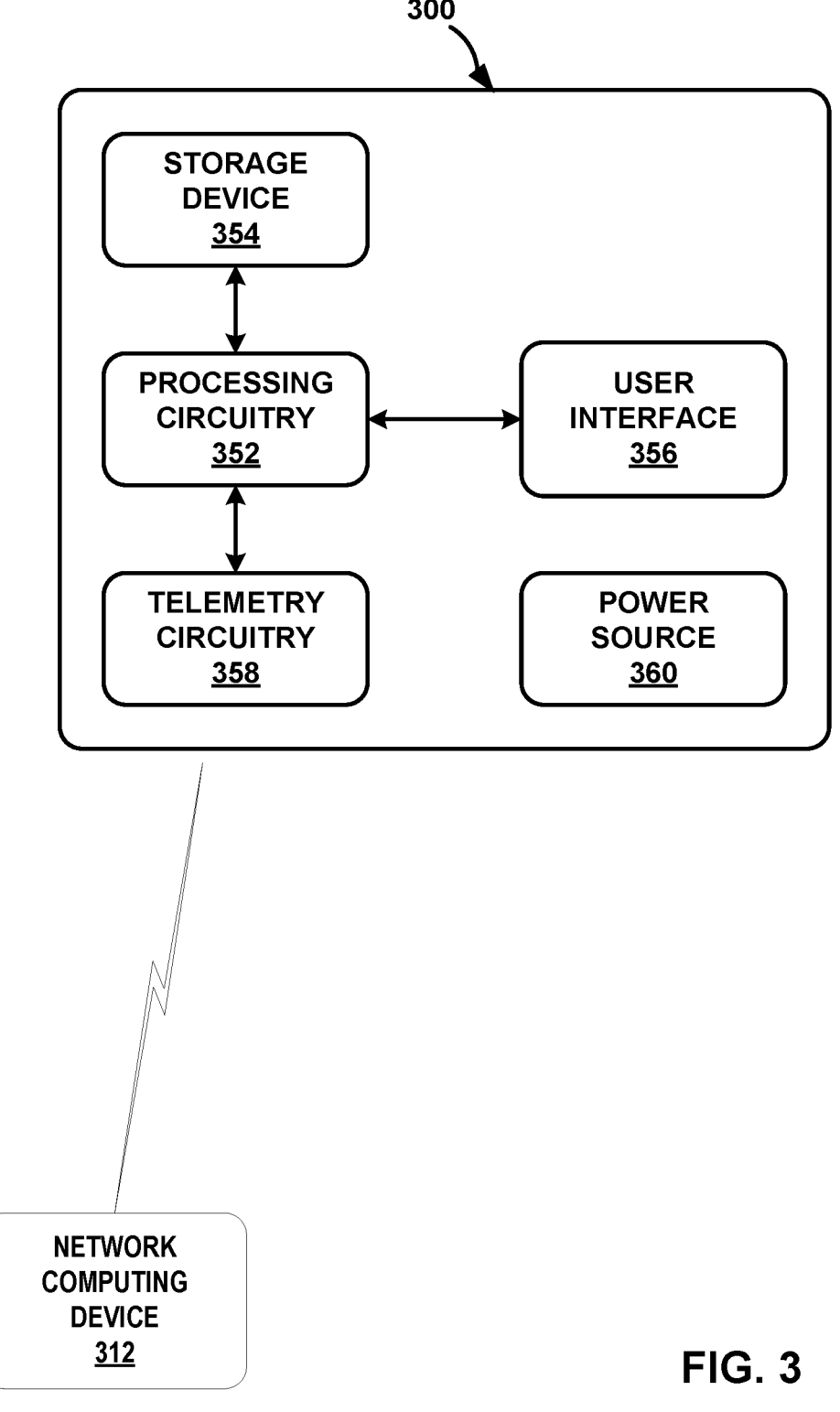
FIG. 3 is a block diagram illustrating an example configuration of components of the external programmer of FIG. 1, in accordance with one or more techniques of this disclosure.

FIG. 3 is a block diagram illustrating an example configuration of components of external computing device 300, in accordance with one or more techniques of this disclosure. External computing device 300 may be an example of external computing device 150 of FIG. 1. Although external computing device 300 may generally be described as a hand-held device, external computing device 300 may be a larger portable device or a more stationary device. In addition, in other examples, external computing device 300 may be included as part of an external charging device or include the functionality of an external charging device. As illustrated in FIG. 3, external computing device 300 may include processing circuitry 352, storage device 354, user interface 356, telemetry circuitry 358, and power source 360. Storage device 354 may store instructions that, when executed by processing circuitry 352, cause processing circuitry 352 and external computing device 300 to provide the functionality ascribed to external computing device 300 throughout this disclosure. Each of these components, circuitry, or modules, may include electrical circuitry that is configured to perform some, or all of the functionality described herein. As described above in relation to FIG. 1, processing circuitry 352 may communicated with network computing device 312. In some examples, processing circuitry 352 may transfer any stored data in a memory connected to processing circuitry 352, e.g., storage device 354, to another computing device for review or further processing, such as to network computing device 312. Network computing device 312 is an example of network computing device 112 described above in relation to FIG. 1.

In general, external computing device 300 includes any suitable arrangement of hardware, alone or in combination with software and/or firmware, to perform the techniques attributed to external computing device 300, and processing circuitry 352, user interface 356, and telemetry circuitry 358 of external computing device 300. In various examples, external computing device 300 may include one or more processors, such as one or more microprocessors, DSPs, ASICs, FPGAs, or any other equivalent integrated or discrete logic circuitry, as well as any combinations of such components. External computing device 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external computing device 300 to provide the functionality ascribed to external computing device 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines stimulation pulses, such as control pulses and/or informed pulses. Storage device 354 may also store data received from a medical device (e.g., IMD 110). For example, storage device 354 may store stimulation signal and/or ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 358 may support wireless communication between the medical device and external computing device 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external computing device 300 and IMD 110 include RF communication according to the 802.11 or Bluetooth® specification sets or other standard or proprietary telemetry protocols. In this manner, other external devices may be capable of communicating with external computing device 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external computing device 300 provides visual, audible, and/or tactile notifications that indicate there are new instructions. External computing device 300 requires receiving user input acknowledging that the instructions have been completed in some examples.

According to the techniques of the disclosure, user interface 356 of external computing device 300 receives an indication from a clinician instructing a processor of the medical device to update one or more therapy stimulation programs or to update one or more test stimulation programs. Updating therapy stimulation programs and test stimulation programs may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including control pulses and/or informed pulses to commence or to cease.

Power source 360 is configured to deliver operating power to the components of external computing device 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external computing device 300. In other examples, traditional batteries (e.g., nickel cadmium or lithium ion batteries) may be used. In addition, external computing device 300 may be directly coupled to an alternating current outlet to operate.

Figure 4:
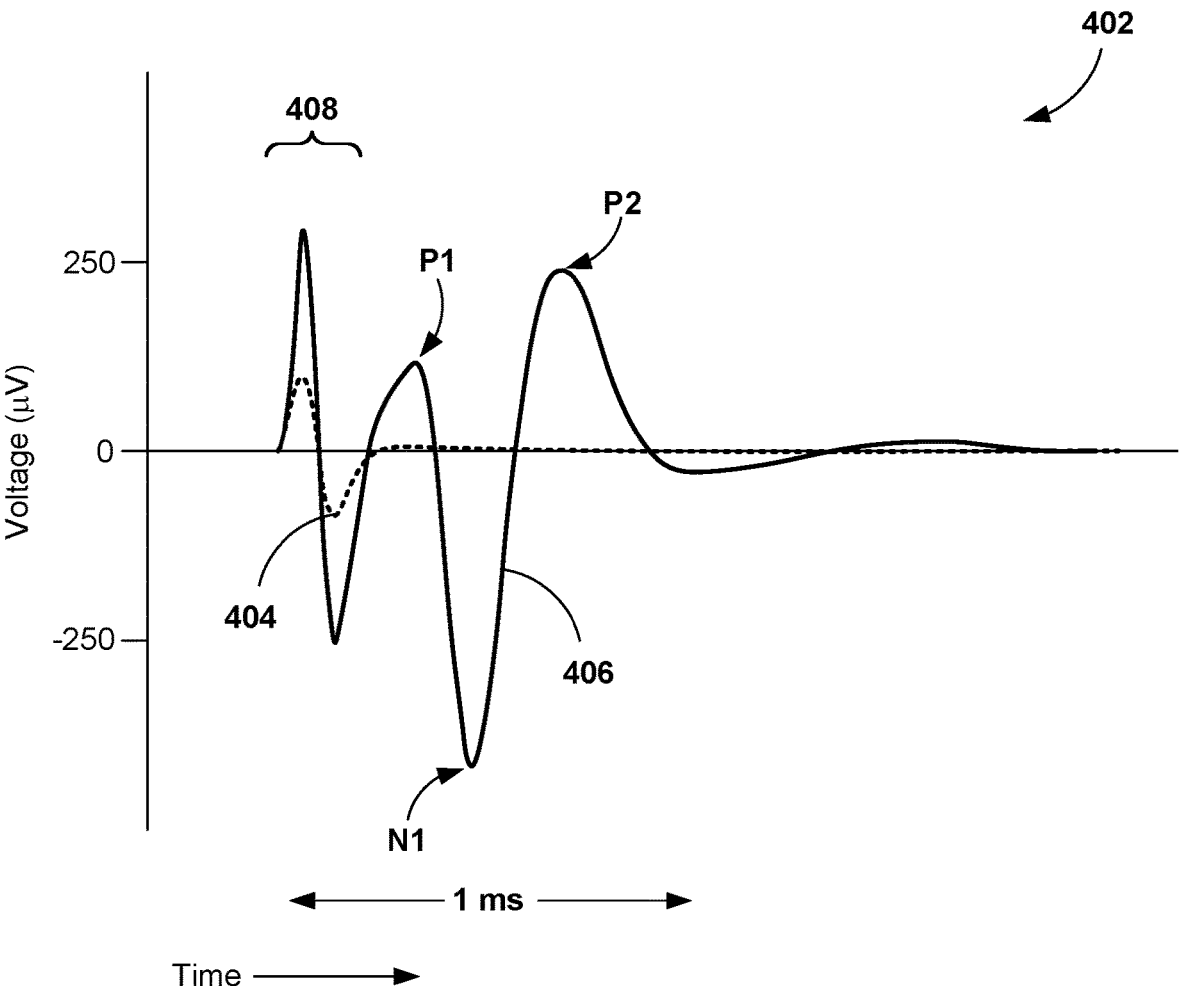
FIG. 4 is a time graph of example evoked compound action potentials (ECAPs) sensed for respective stimulation pulses, in accordance with one or more techniques of this disclosure.

FIG. 4 is a time graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from stimulation pulses (e.g., a control pulse) that were delivered from a guarded cathode, where the stimulation pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse, or a stimulation pulse which results in no detectable ECAP. It is noted that monophasic, tri-phasic, or pulses with another quantity of phases may be in other examples.

Sensing circuitry of an IMD, e.g., IMD 110 and IMD 200 of FIGS. 1 and 2, may detect peaks 408 of ECAP signal 404. Peaks 408 represent stimulation signals of the delivered stimulation pulse. However, no propagating signal is detected after the stimulation signal in ECAP signal 404 because the stimulation pulse had an intensity (e.g., an amplitude and/or pulse width) that was "sub-threshold" or below a detection threshold (e.g., a sub-detection threshold) and/or below a propagation threshold (e.g., a sub-propagation threshold).

In contrast to ECAP signal 404, ECAP signal 406 represents the voltage amplitude detected from a supra-detection stimulation threshold stimulation pulse. Peaks 408 of ECAP signal 406 are detected and represent stimulation signals of the delivered stimulation pulse. After peaks 408, ECAP signal 406 also includes peaks P1, N1, and P2, which are three typical peaks representative of propagating action potentials from an ECAP. The example duration of the stimulation signal and peaks P1, N1, and P2 is approximately 1 millisecond (ms).

When detecting the ECAP of ECAP signal 406, different characteristics may be identified. For example, the characteristic of the ECAP may be the amplitude between N1 and P2. This N1-P2 amplitude may be detectable even if the stimulation signal impinges on P1, a relatively large signal, and the N1-P2 amplitude may be minimally affected by electronic drift in the signal. In other examples, the characteristic of the ECAP used to control subsequent stimulation pulses (e.g., control pulses and/or informed pulses) may be an amplitude of P1, N1, or P2 with respect to neutral or zero voltage. In some examples, the characteristic of the ECAP used to control subsequent stimulation pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2.

The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the stimulation pulse, as long as the pulse amplitude is greater than threshold such that nerves depolarize and propagate the signal. The target ECAP characteristic (e.g., the target ECAP amplitude) may be determined from the ECAP signal detected from a stimulation pulse (or a control pulse) when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change therapy pulse parameter values and maintain the target ECAP characteristic value during therapy pulse delivery.

Figure 5:
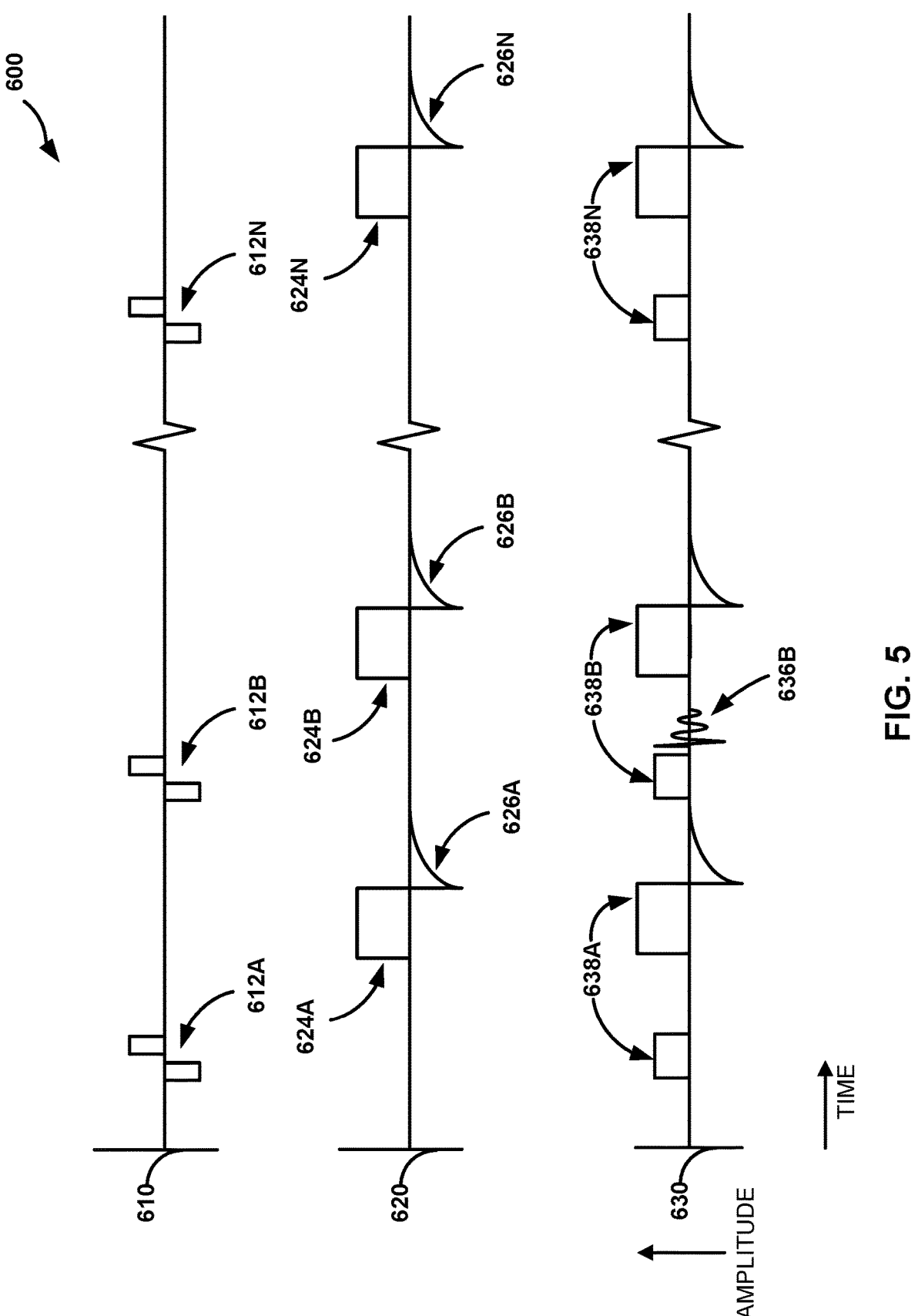
FIG. 5 is an example timing diagram illustrating one example of electrical stimulation pulses, respective stimulation signals, and respective sensed ECAPs, in accordance with one or more techniques of this disclosure.

FIG. 5 is a timing diagram 600 illustrating one example of electrical stimulation pulses, respective stimulation signals, and respective sensed ECAPs, in accordance with one or more techniques of this disclosure. For convenience, FIG. 5 is described with reference to IMD 200 of FIG. 2. As illustrated, timing diagram 600 includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation signals 638A-638N (collectively "stimulation signals 638").

In the example of timing diagram 600 of control pulse 612A and control pulse 612N do not evoke an ECAP that is detectible by IMD 200. Although control pulse 612B emits ECAP 636B, which is detectible by IMD 200, it may be the case that IMD 200 does not sense enough detectible ECAPs for therapy determination in the example of FIG. 5. As such, IMD 200 may determine one or more characteristics of stimulation signals 638 in order to determine one or more parameters of upcoming stimulation pulses following control pulse 612N. For example, IMD 200 may determine an amplitude of at least a portion of each stimulation signal of stimulation signals 638 and determine the one or more parameters of the upcoming stimulation pulses based on the determined amplitudes. Although stimulation signals 638 are illustrated as square pulses, stimulation signals 639 may include other shapes and/or waveforms, in some examples. In some examples, each stimulation signal of stimulation signals 638 may include two or more phases. Processing circuitry 210 of IMD 200 may analyze the two or more phases of stimulation signals 638 in order to determine therapy.

Figure 6A:
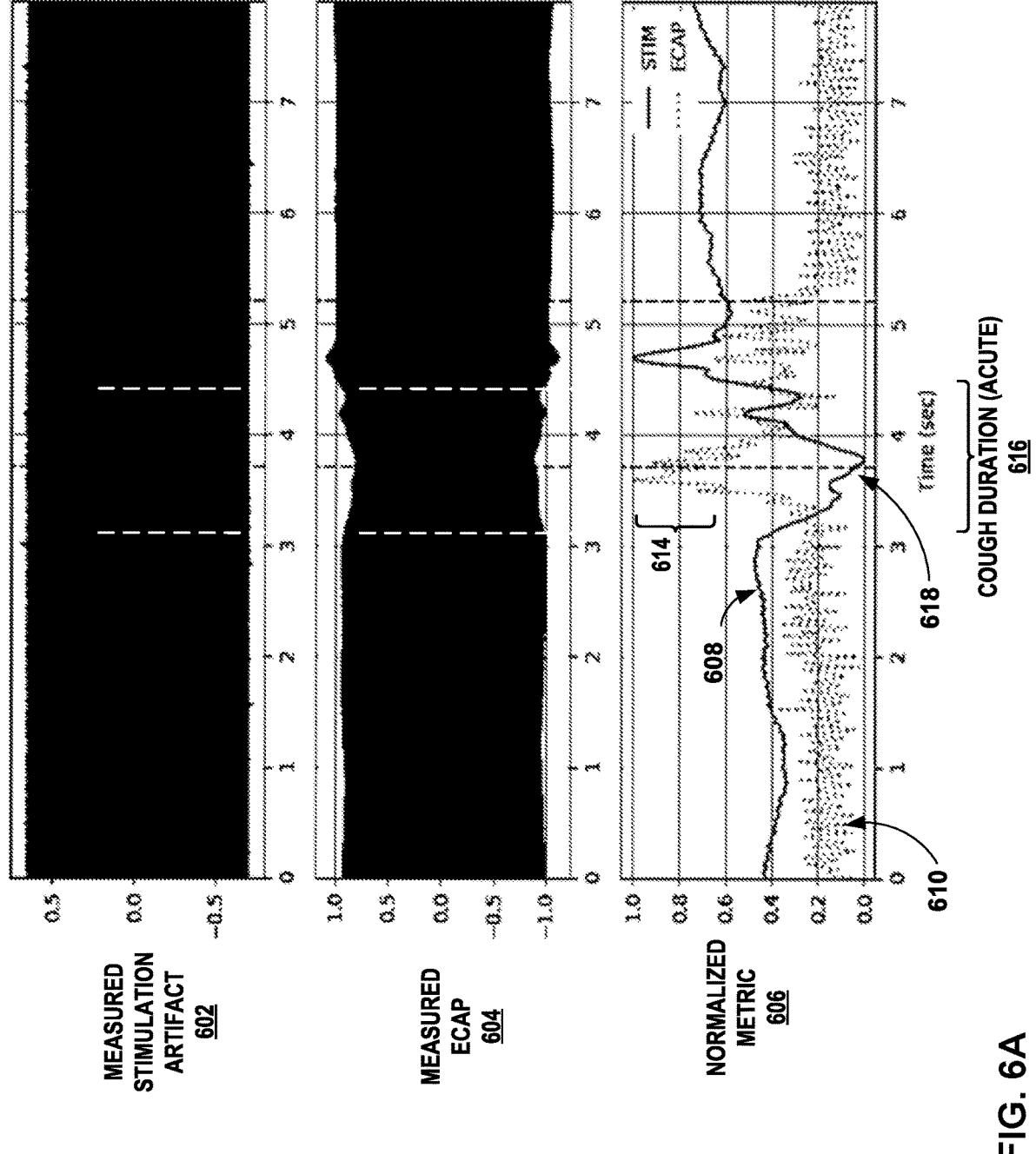
FIG. 6A is a time graph illustrating the effect of an aggressor on the stimulation artifact and measured ECAP.

FIG. 6A is a time graph illustrating the effect of an aggressor on the stimulation artifact (e.g., the sensed delivered electrical stimulation or electric field imaging) and measured ECAP (e.g., the sensed physiological response to the stimulus). As noted above, sensing the stimulation artifact may also be referred to as electrical field imaging in this disclosure. Processing circuitry of a medical device may also be configured to measure the stimulation artifact as well as to measure ECAP to provide closed loop feedback to the system. ECAP stimulation may use a larger stimulation pulse to generate the ECAP than the magnitude of the stimulation pulse needed to deliver electrical stimulation that may be measurable to be used for therapy feedback. In some examples, the system may use the stimulation artifact for feedback, which may reduce output stimulation power and thereby reduce battery consumption when compared to using ECAP alone for feedback.

An aggressor is an event or action by the patient that may change the perceived stimulation and may be conscious or unconscious on the part of the patient. Some example aggressors may include coughing, laughing, changing posture, or some other movement, changes in blood chemistry, hydration levels and so on. In some examples, an aggressor may increase or decrease the measured ECAP and therefore be an event an event impacting therapy.

The measured stimulation artifact 602 time chart shows a consistent amplitude over the time period shown. Individual stimulation events may not be visible in measured stimulation artifact 602 because the time scale is of FIG. 6A is large relative to the stimulation repetition rate.

Stimulation graph 608 and ECAP graph 610 in normalized metric chart 606 depict an envelope of measured stimulation artifact 602 and measured ECAP 604. In other examples, sensing circuitry 206, described above in relation to FIG. 1, may receive the sensed signals and determine an impedance at an electrode, e.g., based on an output stimulation current and a measured amplitude. In some examples, processing circuitry 210 may further analyze the received signals by determining serialization impedance, polarization impedance, voltage, measured frequency, measure over the time of stimulation, and other components of the received signal. Depending on the desired measurement, a stimulation pulse may be characterized as a low amplitude with a long pulse width, which may show changes in slope or other signal differences over the duration of the stimulation. In other examples, the stimulation may be characterized by a higher, sub-threshold, amplitude with a shorter pulse width to detect other characteristics of the simulation artifact. In some examples the stimulation pulse may be a biphasic pulse and may be shaped as a square wave, triangular wave, exponentially decreasing slope, and other shapes to elicit different types of stimulation artifact.

The example of FIG. 6A depicts the impact of an aggressor on the stimulation artifact as well as the ECAP, e.g., cough 616 over a short, or acute duration. During 616, the patient performs a movement, in the example of FIG. 6A, the movement is a seated cough. The increase in ECAP magnitude (614) may be caused by the stimulation electrodes moving closer to the target nerve because of the aggressor, e.g., a seated cough in the example of FIG. 6A. At the same time, the stimulation artifact shows a change (618) caused by the aggressor. In some examples, the system may train the use of the stimulation artifact as a feedback variable for adjusting subsequent stimulation based on the ECAP values themselves. In any event, the system may monitor the stimulation artifact, or electrical field values, and adjust one or more stimulation parameter values to maintain effective therapy.

Figure 6B:
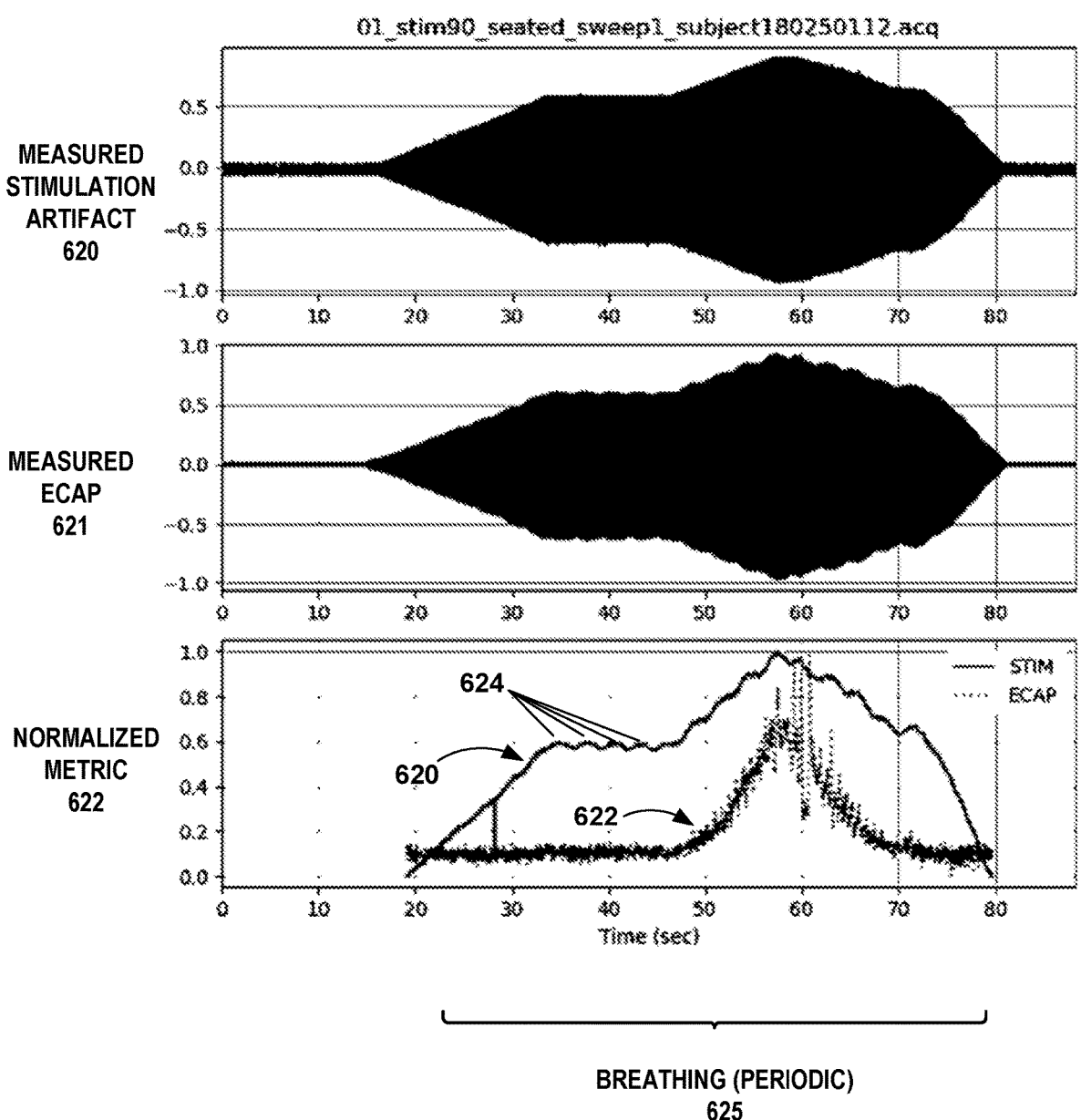
FIG. 6B is a time graph illustrating the effect of patient breathing on the stimulation artifact and measured ECAP.

FIG. 6B is a time graph illustrating the effect of patient breathing on the stimulation artifact and measured ECAP. Some measured characteristics of the sensed delivered stimulation and the ECAP may increase or decrease (e.g., track) an increase or decrease of the delivered stimulation. For example, the measured magnitude of sensed delivered stimulation and the magnitude of the ECAP may correlate to the magnitude the delivered stimulation. In the example of FIG. 6B, the increased amplitude of ECAP 622 and the sensed delivered stimulation 620 track with an increase, up to time 58 seconds, and decrease, after 60 seconds, of the magnitude of the delivered electrical stimulation.

Breathing may be a periodic event impacting therapy 625. While the ECAP 622 may change somewhat with patient breathing, the example of FIG. 6B sensed delivered stimulation 620 provides an indicator of the breathing of the patient, as shown by ripples 624.

Figure 6C:
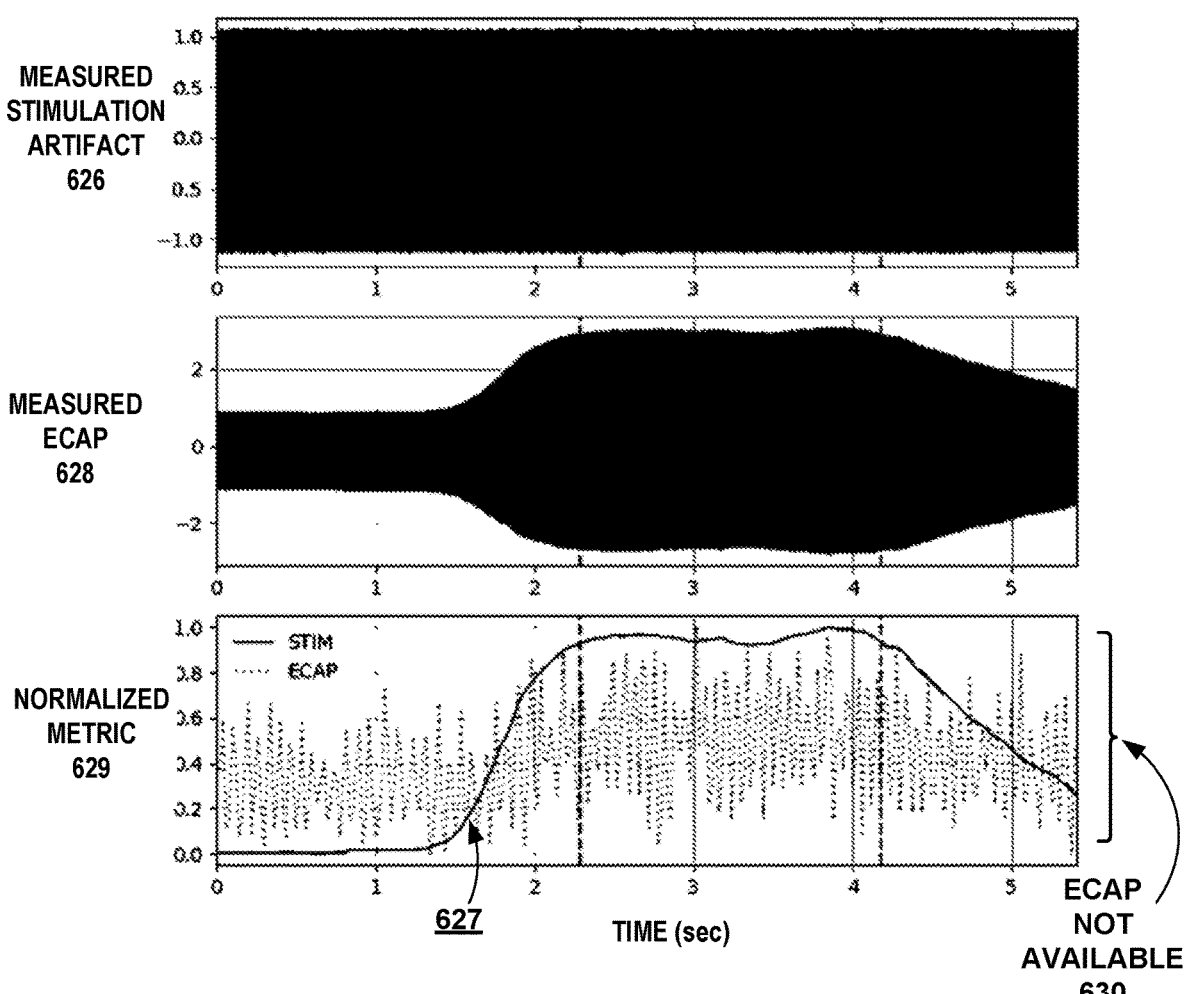
FIG. 6C is a time graph illustrating the effect of patient posture on the stimulation artifact and measured ECAP.

FIG. 6C is a time graph illustrating the effect of patient posture on the stimulation artifact and measured ECAP. FIG. 6C depicts an antidromic study of a patient's back arching movement, as the aggressor in graphs 626, 628 and 629.

In an orthodromic study, the recording electrodes measure the action potential traveling in the physiologic direction. In an antidromic study, the recording electrodes measure the action potential traveling opposite the physiologic direction. The measured magnitude of sensed delivered stimulation may track with aggressors even in cases with no ECAPs. The patient's posture, e.g., an arched back as in the example of FIG. 6C, may cause the electrode position to move relative to the target nerve such that an ECAP is not available (630) as shown in graph 629. However, changes in the stimulation artifact 627 may change as the patient's posture changes, e.g., increasing or decreasing the degree of back arch.

Figure 6D:
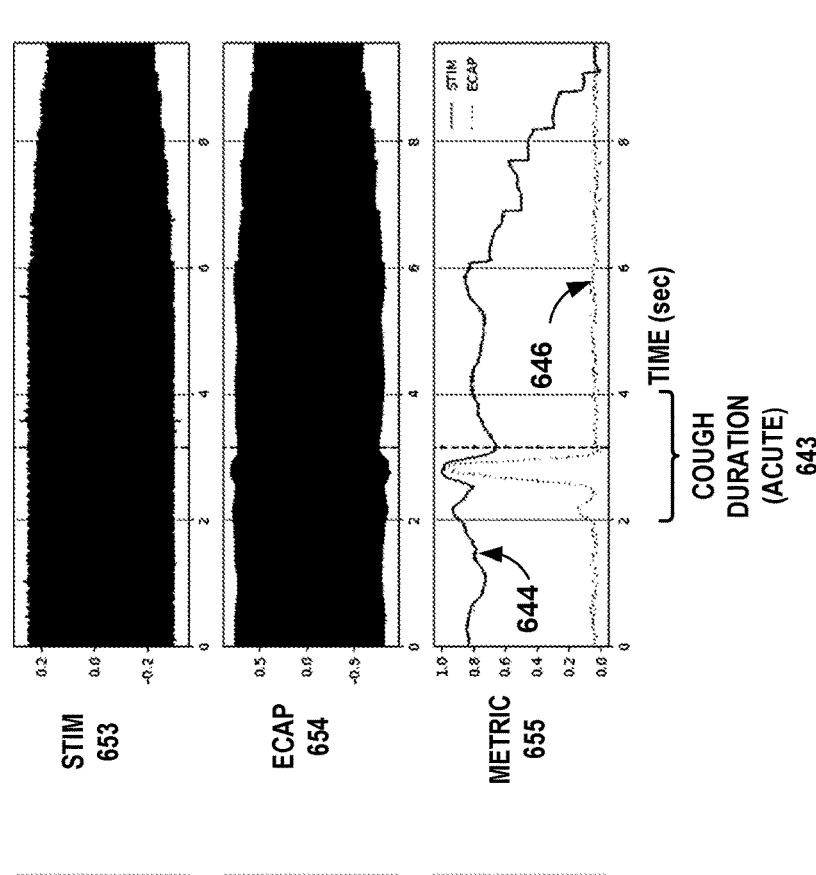
FIG. 6D is a time graph illustrating the effect of patient coughing and lead position on the stimulation artifact and measured ECAP.
Figure 6D:
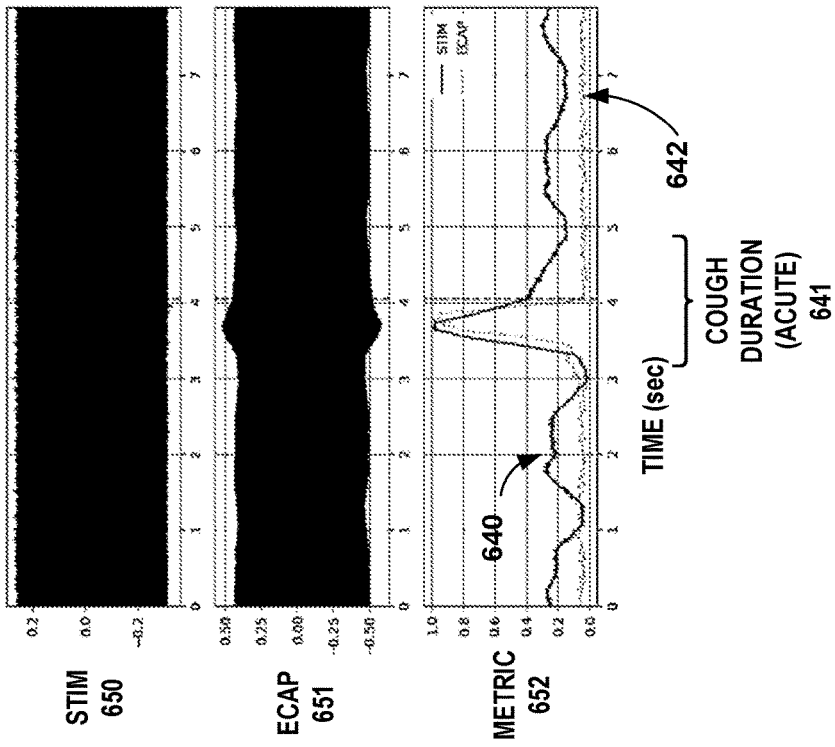

FIG. 6D is a time graph illustrating the effect of patient coughing and lead position on the sensed delivered stimulation and measured ECAP. The sensed delivered stimulation may be sensitive to the proximity between stimulation output and sensing/recording electrodes. The stimulation and recording electrodes for graphs 653, 654 and 655 may be closer together than for graphs 650, 651 and 652. For example, for the electrode arrangement described above in relation to FIG. 2, graphs 653, 654 and 655 may stimulate using the B electrode of 232 and record using the C electrode of 232. In contrast, graphs 650, 651 and 652 may stimulate using the A electrode of 232 and record using the D electrode of 232. This example is just one possibility. Other electrode combinations may have been used to capture the data shown in FIG. 6D.

FIG. 7 is a graph illustrating growth curves for the sensed delivered stimulation and measured ECAP for sub-sensory electrical stimulation delivery dosage. The growth curves depict the measured value of the stimulation artifact 702 and measured ECAP 704 as the stimulation level increases. The growth curves in the example of FIG. 7, show how the stimulation artifact 702 and the measured ECAP 704 changes vs the stimulation level. The example of FIG. 7 depicts during open loop testing, how aggressors may move in amplitude along the Y-axis. The example of FIG. 7 is similar to the seated cough aggressor depicted in graphs 650, 651 and 652 of FIG. 6D.

The example of FIG. 7, as well as FIG. 12A described below, also show that electric field imaging growth curves (702) is sloped, approximately linearly, along the entire span of stimulation current. In contrast, the ECAP growth curve (704) is flat at the low end of the stimulation current. The flat area of the ECAP growth curve 704 may make detecting changes in the ECAP based on changes in the stimulation current challenging to detect, for low amplitude stimulation current. In contrast, in the example of FIG. 7, the electric field imaging growth curve 702 may provide a control signal that is response across the range of stimulation current shown in FIG. 7.

FIGS. 8-11 present data collected comparing using the sensed delivered stimulation for subsensory dose control, compared to measured ECAP data, under the same conditions. Some examples in FIGS. 8-11 may correlate to the examples described above in relation to FIGS. 6A-6D. As described above, the ECAP may be used to provide feedback to for dose control for electrical stimulation therapy delivered by IMD 110 and IMD 200 described above in relation to FIGS. 1 and 2. In some examples, some patients may feel the control pulses used to evoke an ECAP, which depending on the patient, may cause not discomfort, or be perceived as annoying to painful. Measuring the stimulation artifact may be a desirable technique to provide subsensory dose control. In some examples, patients may not sense the delivered electrical stimulation therapy that evokes the stimulation artifact because the intensity/dosage may be less that a perception threshold of a patient, as described above.

Figure 8:
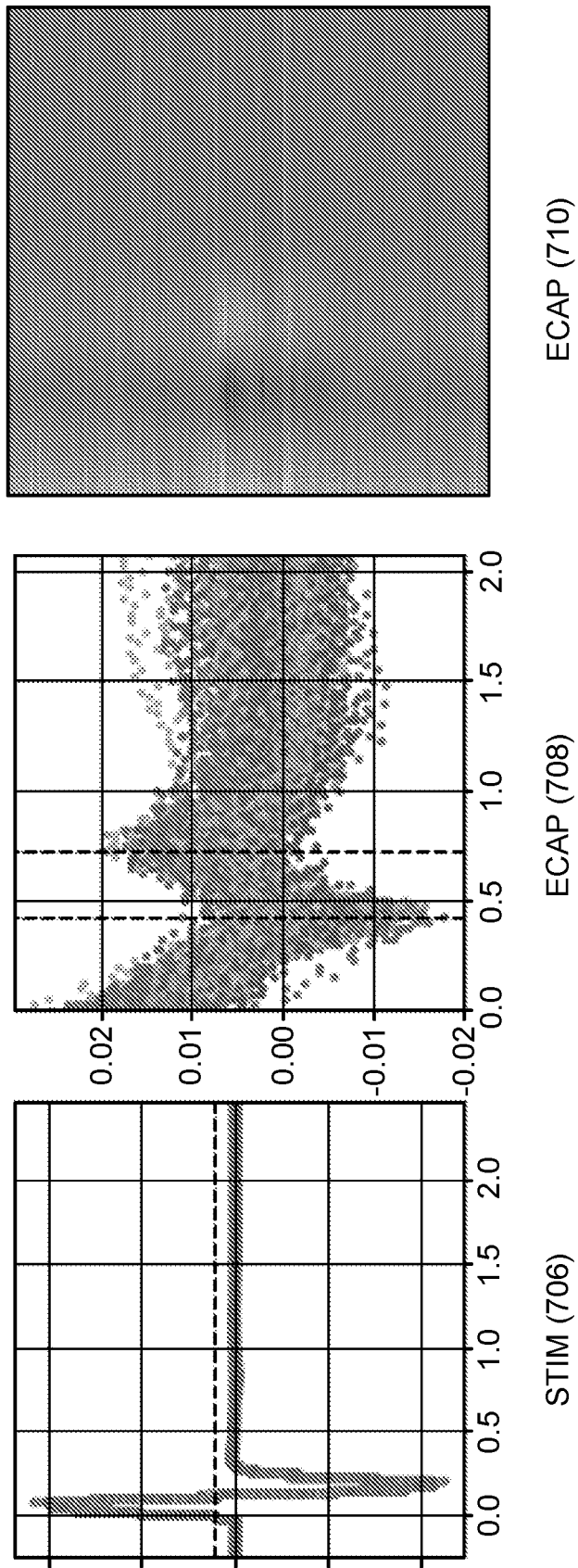
FIG. 8 is a time graph illustrating the effect of a seated cough on the stimulation artifact and measured ECAP.

FIG. 8 is a time graph illustrating the sensitivity of the sensed delivered stimulation compared to a measured ECAP for an aggressor. The aggressor in the example of FIG. 8 is a seated cough, which may be similar to the seated cough described above in relation to FIG. 6A.

The information shown in FIG. 8 is based on data collected using both open loop and closed loop stimulation. Comparing the stimulation artifact 706 data to the ECAP data 708 and 710, shows the ECAP data 708 may have more variation than the stimulation artifact data 706 from test run to test run. In addition, that data presented in FIG. 8 shows that the stimulation artifact 706 may be measurable, even with patients with poor ECAP response. In this manner the stimulation artifact 706 may be more sensitive in some examples when compared to an ECAP response. Note that in 710, the dark areas indicate a negative transition for the ECAP, while the lighter areas indicate a positive transition.

Figure 9:
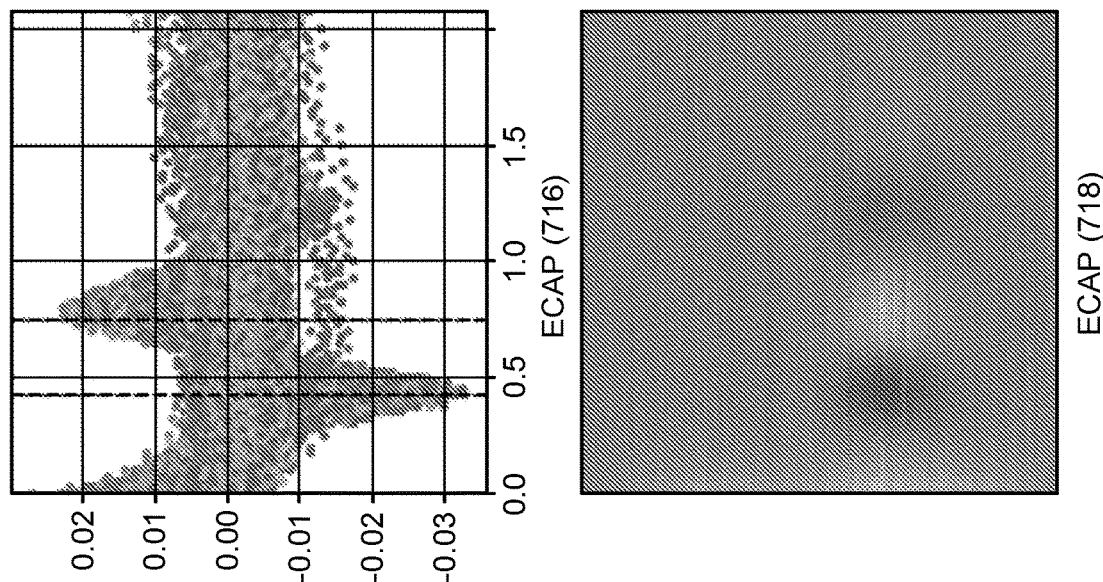
FIG. 9 is a time graph illustrating the effect of the stimulation artifact and ECAP as the stimulation amplitude changes.
Figure 9:
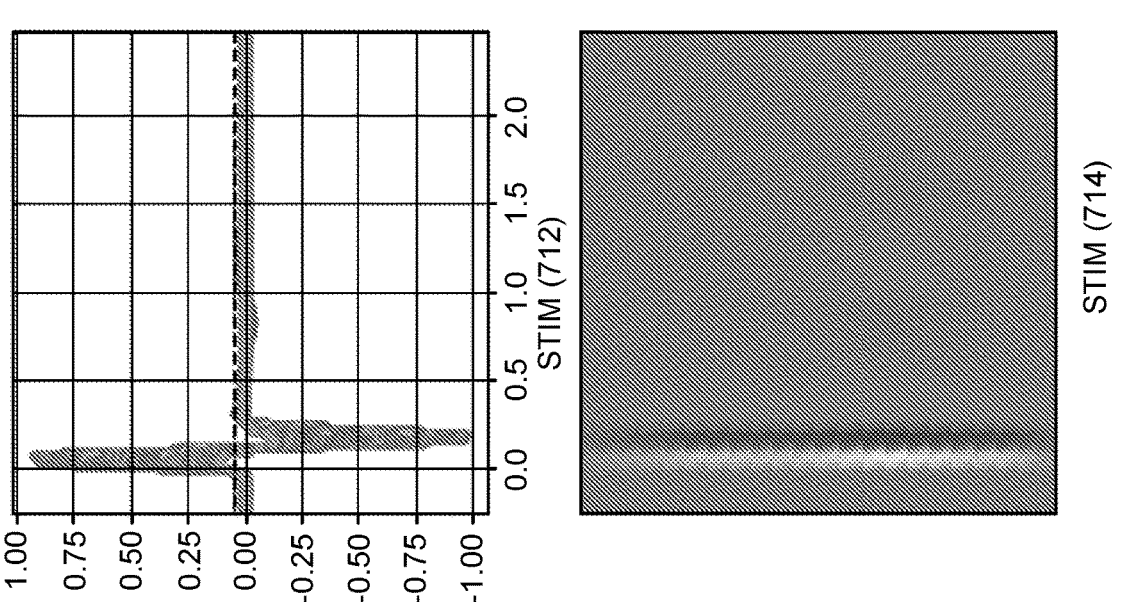

FIG. 9 is a time graph illustrating the effect of the sensed delivered stimulation and ECAP as the stimulation amplitude changes. The example of FIG. 9 correlates to the breathing example described above in relation to FIG. 6B. As described above in relation to FIG. 8, the ECAP data 716 may have more variation than the stimulation artifact data 712. Also, in stimulation graph 714 and ECAP graph 719, the dark areas indicate a negative transition, while the lighter areas indicate a positive transition.

Figure 10:
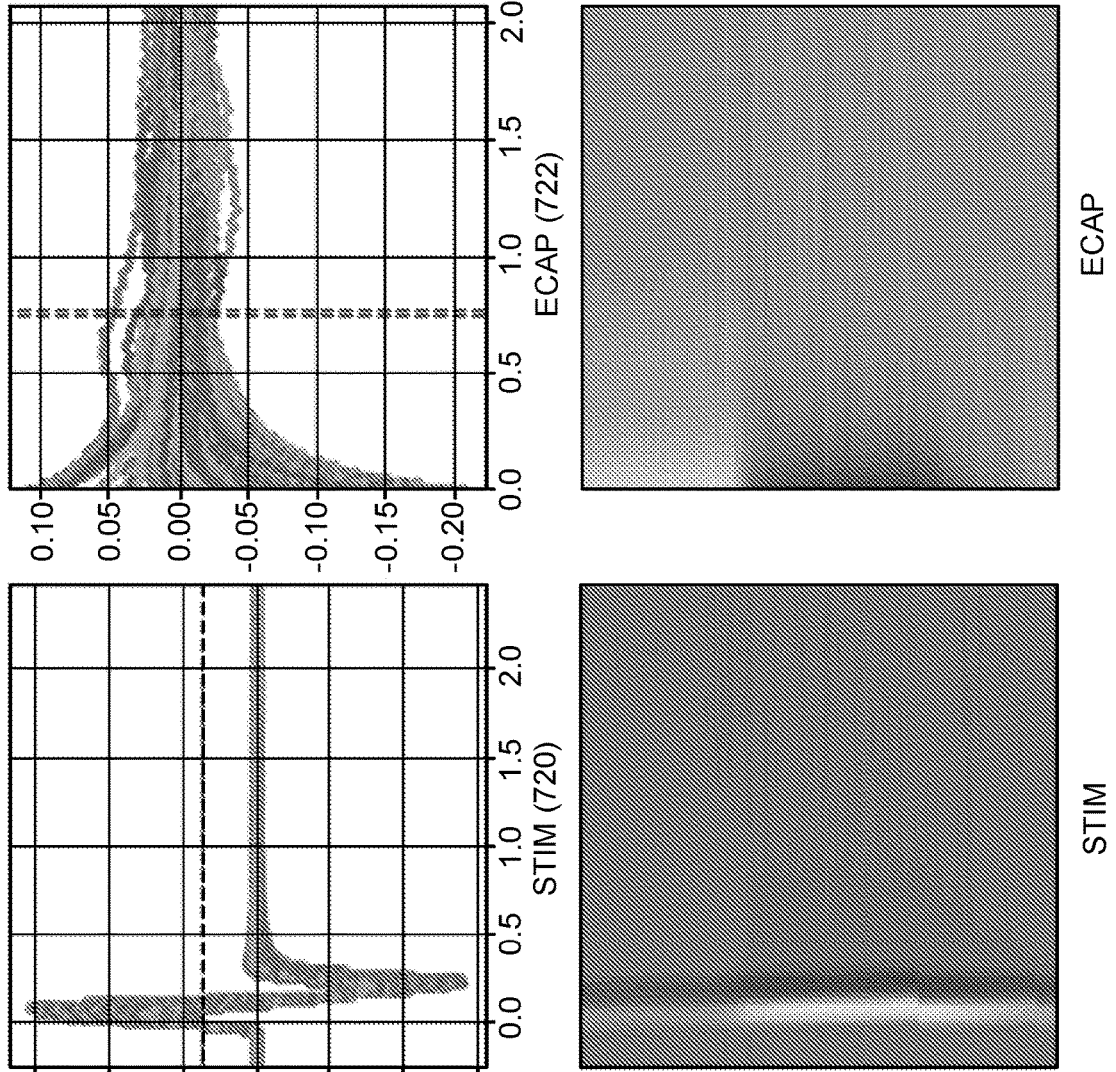
FIG. 10 is a time graph illustrating the effect of aggressors on the stimulation artifact and measured ECAP.

FIG. 10 is a time graph illustrating the effect of patient posture as an aggressor on the sensed delivered stimulation and measured ECAP. FIG. 10 correlates with the changes in patient posture as described above in relation to FIG. 6C, in which the sensed delivered stimulation (stimulation artifact) may track with the aggressor, e.g., changes in the back arch position, even when ECAPs are not available. The variation in the ECAP graph 722 is much larger than for the sensed delivered stimulation 720, which may indicate that using the stimulation artifact to track an aggressor may provide more consistent results than using ECAP measurements.

Figure 11:
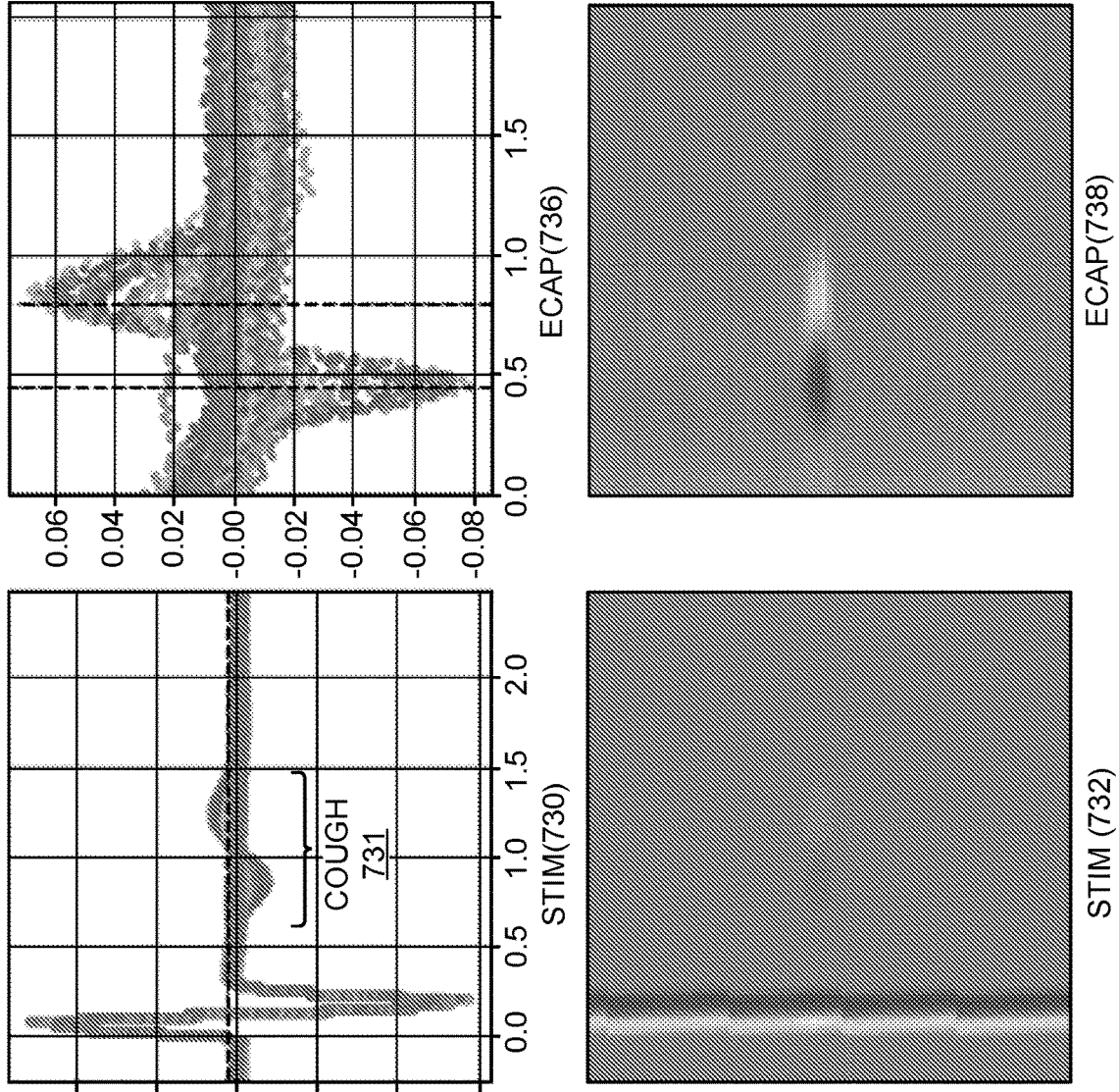
FIG. 11 is a time graph illustrating the effect of aggressors on the stimulation artifact and measured ECAP.

FIG. 11 is a time graph illustrating the effect of aggressors on the sensed delivered stimulation and measured ECAP. The data shown by FIG. 11 correlates with the seated cough depicted in graphs 650, 651 and 652 of FIG. 6D. The data shown by FIG. 11 is another example of how the stimulation artifact may track with an aggressor, such as a cough, as described above in relation to FIGS. 8, 9 and 10. The stimulation artifact, as shown in graphs 730 and 732, may detect the presence of an aggressor, like cough 731. In ECAP graphs 736 and 738, it may be more difficult to detect cough 731, which is also shown as 641 in FIG. 6D.

Figure 12B:
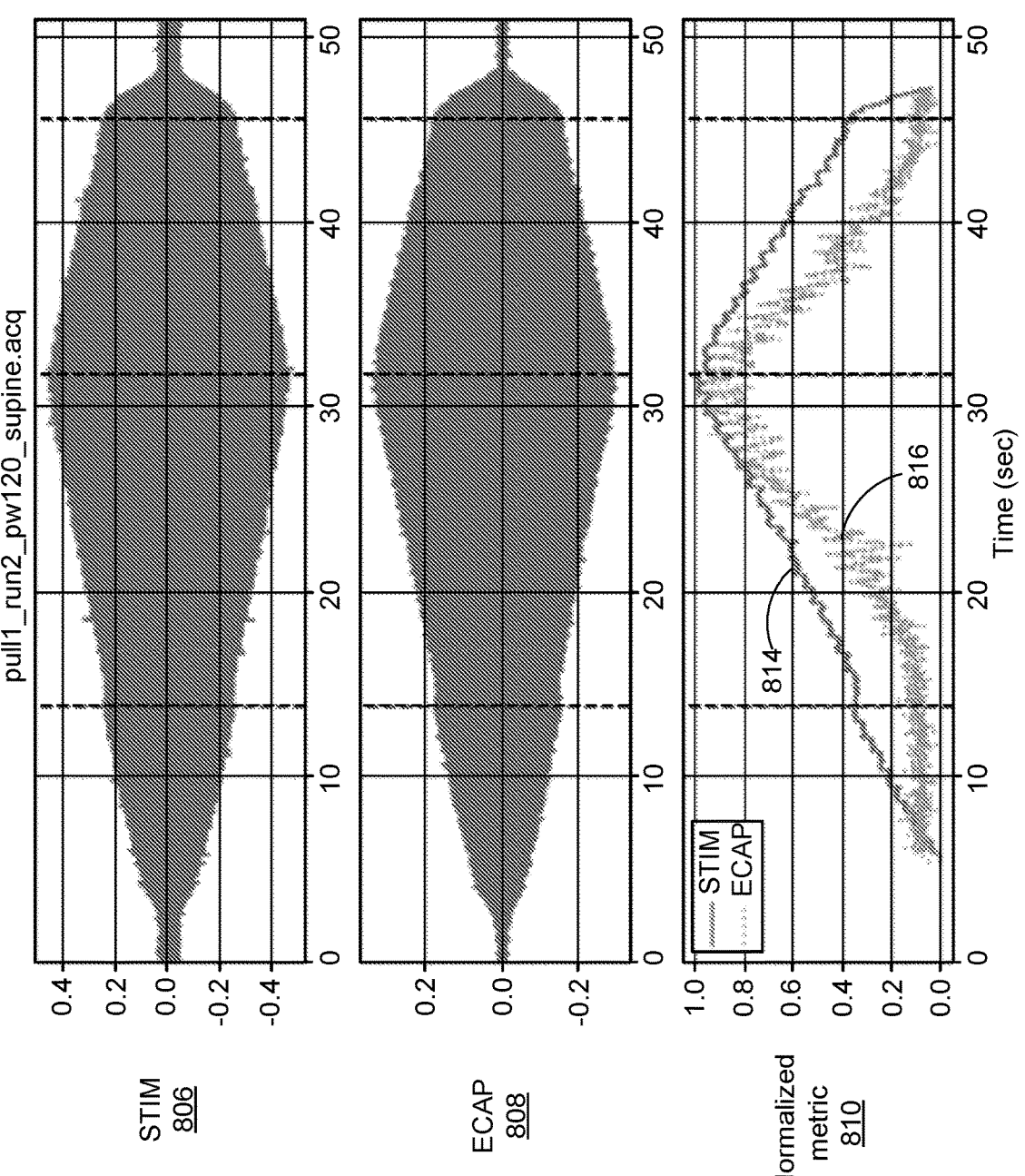
Figure 12C:
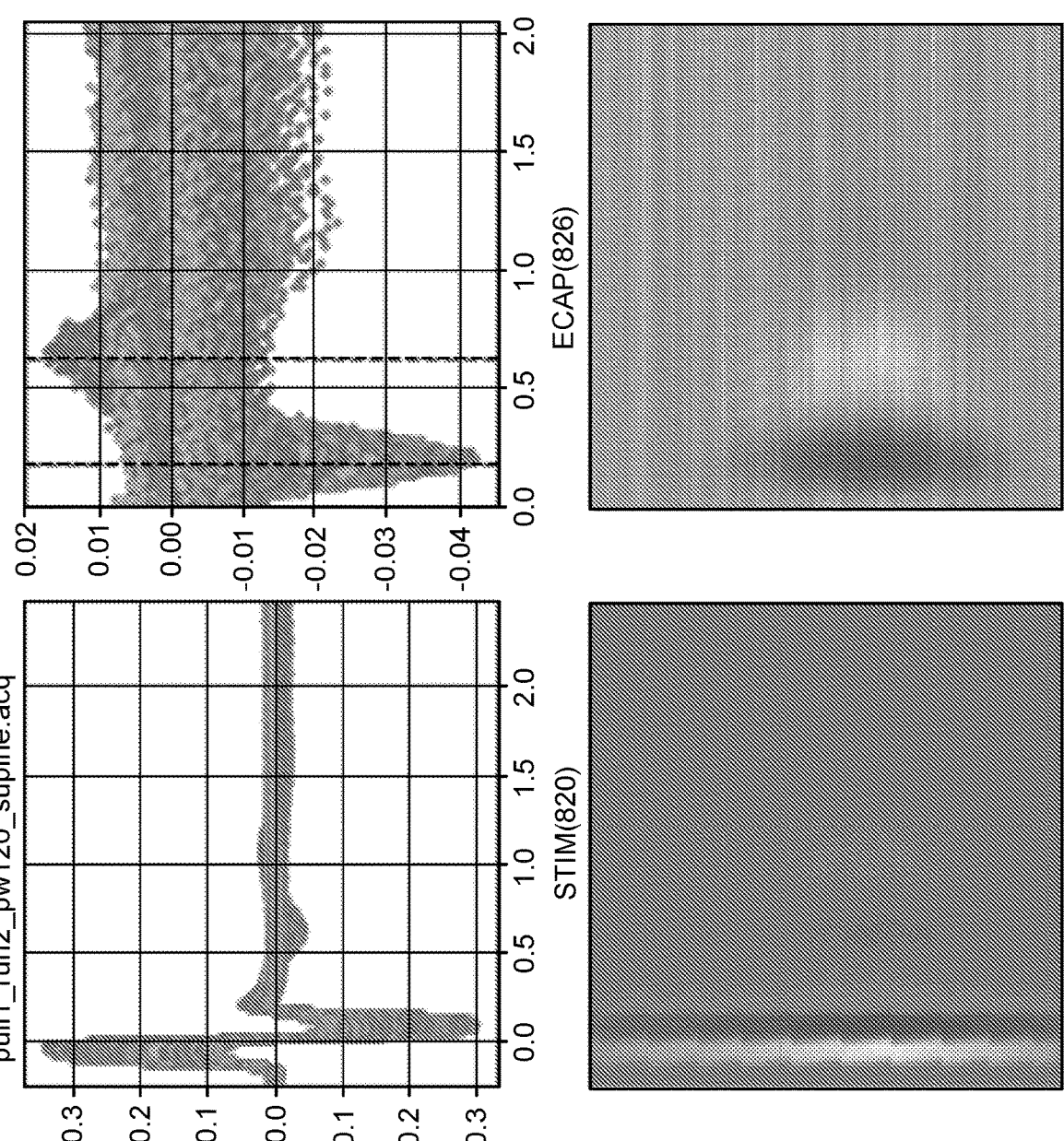

FIGS. 12A, 12B and 12C are graphs illustrating growth curves of the sensed delivered stimulation and measured ECAP. In the example of FIGS. 12A-12C, the patients were in a supine position. The growth curves of FIG. 12A show how the stimulation artifact and the measured ECAP changes as the stimulation level increases. The sensed delivered stimulation 802 presents a linear relationship with the change in stimulation amplitude while the ECAP 804 growth curve show a non-linear relationship as well as more variation when compared to the sensed delivered stimulation 802.

FIG. 12B shows the stimulation increasing and decreasing over time, and the resultant changes in sensed delivered stimulation and ECAP. The sensed delivered stimulation 806 and ECAP 808 respond in a similar manner as the delivered stimulation amplitude is increase, up to the 32 second mark, and decreased for the remainder of the test run. The normalized metric 810 graph shows increased variation in the ECAP 816 when compared to the sensed delivered stimulation 814.

FIG. 12C depicts the stimulation artifact and ECAP timing after delivery of the stimulation pulse. The example of FIG. 12C depicts a selected set of test runs from a growth curve in the example of FIG. 12A. As described above, the ECAP 826 shows increase variation when compared to the sensed delivered stimulation 820.

Figure 13A:

FIGS. 13A, 13B and 13C are time graphs illustrating a stimulation pulse and the impact of sensed residual phase feedback. FIG. 13A is time graph illustrating a residual phase of a stimulation pulse delivered through two different electrode settings. The example of FIG. 13A includes a stimulation pulses 801. Pulse 812 is a bipolar pulse 808 using two electrodes, e.g., of electrodes 132A and 132B, described above in relation to FIG. 1. Pulse 810 is a multi-polar pulse 806 using three electrodes, The zoomed in view of the residual phase 804 of stimulation pulses 801 show the detail of bipolar pulse 814 and multi-polar pulse 816.

FIG. 13B is a time graph illustrating changes in the residual phase 820 of the electric field imaging as the patient changes posture. FIG. 13C is a time graph illustrating the increased consistency for electric field imaging that includes residual phase feedback.

In operation, a medical device, e.g., IMD 110 described above in relation to FIG. 1, may include stimulation generation circuitry configured to deliver a first stimulation pulse 801 to a patient, e.g., patient 105, as shown in FIG. 13A. Sensing circuitry, e.g., sensing circuitry 206 described above in relation to FIG. 2, may be configured to sense residual phase 820 of the first stimulation pulse, e.g., as shown in FIGS. 13A and 13B. Processing circuitry of system 100, of FIG. 1, may be configured to determine that a value of a characteristic of the sensed residual phase of the first stimulation pulse exceeds a target residual phase value 824, or is within or outside of a threshold range (not shown in FIG. 13B). Based on determining that the value of the characteristic of the sensed residual phase exceeds the target residual phase value 824, or is outside or within the threshold range, the processing circuitry may change a first value of a parameter to a second value of the parameter that at least partially defines a second stimulation pulse deliverable by the stimulation generation circuitry after the residual phase of the first stimulation pulse was sensed (e.g. FIG. 13C).

FIG. 14 is a flow diagram illustrating an example operation of the system of this disclosure. A medical device such as IMD 110 and IMD 200 described above in relation to FIGS. 1 and 2 may perform the steps depicted by the blocks of FIG. 14. In some examples, processing circuitry of an external computing device such as external computing device 150 and/or network computing device 112 may perform on or more functions as described above in relation to FIGS. 1-3.

A medical device, e.g., an INS such IMD 110, may include stimulation generation circuitry configured to deliver electrical stimulation to a patient, such as patient 105 of FIG. 1 (90). The parameters of the electrical stimulation may be set for sub-perception threshold therapy (or other sub-threshold therapy) as well as higher dosage stimulation, e.g., stimulation configured to elicit ECAPs. In some examples IMD 110 may sense the delivered electrical stimulation to provide feedback for subsequent therapeutic stimulation. Processing circuitry of system 100, e.g., processing circuitry 210 of FIG. 2, or other processing circuitry in system 100, may configure the delivered electrical stimulation to avoid saturating sensitive measurement circuitry, e.g., sensing circuitry 206 of FIG. 2. In some examples, the processing circuitry may reduce the intensity for delivered electrical stimulation intended for electrical field imaging. In other examples, the processing circuitry may configure low gain sensing, or other techniques as described above in relation to FIG. 1.

Sensing circuitry of IMD 200 may sense the delivered electrical stimulation, e.g., via electrodes 232 and 234 connected to leads 230 of FIG. 2 (92). Processing circuitry 210, may determine the value of one or more characteristics of the sensed delivered stimulation, e.g., amplitude, number of peaks, timing, pulse width and so on (94). Based on the value of the one or more characteristics of the sensed delivered stimulation, the processing circuitry may adjust one or more stimulation parameter values, e.g., current pulse amplitude, frequency, pulse width, burst length, and so on, that at least partially defines subsequent stimulation to be delivered to the patient (96).

In some examples, the system of this disclosure may initially elicit ECAPs to train the IMD 200 to determine which characteristics of the stimulation artifact to use for feedback for future stimulation, as described above in relation to FIG. 6A. For example, external computing device 150 may cause IMD 200 to deliver stimulation that elicits ECAPs. The system may adjust the delivered stimulation to until the desired combination of stimulation parameters and selected electrodes results in the desired ECAP. The system may also measure the stimulation artifact and determine which characteristics in the measured stimulation artifact correlate with the stimulation that elicited the desired ECAPs. The system may then deliver the stimulation therapy and use the stimulation artifact as feedback to make adjustments to future stimulation therapy.

In one or more examples, the functions described above may be implemented in hardware, software, firmware, or any combination thereof. For example, the various components of FIGS. 1-3, such as network computing device 112, processing circuitry 210, communication circuitry 208, sensing circuitry 206, processing circuitry 352 and so on may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, such as storage device 212 and storage device 354, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache). By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor" and "processing circuitry," as used herein, such as ECS controller 202, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The techniques of this disclosure may also be described by the following examples.

Example 1. A medical device comprising stimulation generation circuitry configured to deliver electrical stimulation to a patient; sensing circuitry configured to sense the delivered electrical stimulation; and processing circuitry operatively coupled to a memory, the processing circuitry configured to: determine the value of one or more characteristics of the sensed delivered stimulation; and based on the value of the one or more characteristics of the sensed delivered stimulation, adjust a stimulation parameter value that at least partially defines subsequent stimulation to be delivered to the patient.

Example 2: The medical device of example 1, wherein the electrical stimulation comprises an electrical current pulse.

Example 3: The medical device of any of examples 1 and 2, wherein the processing circuitry is configured to sense an event impacting therapy based on the value of the one or more characteristics of the sensed delivered stimulation.

Example 4: The medical device of example 3, wherein the event impacting therapy comprises one or more types, the types comprising an acute event, a periodic event, or other event.

Example 5: The medical device of examples 1-4, wherein: the acute event comprises: a patient cough, a patient sneeze, and a patient laugh; the periodic event comprises: the patient's breathing, and the patient sleeping; the other event comprises: the patient's posture change, a blood chemistry change; an electrode environment change and a longitudinal lead movement.

Example 6: The medical device of any combination of examples 1-5, wherein the delivered electrical stimulation comprises a first stimulation pulse and a second stimulation pulse, wherein a magnitude of the second stimulation pulse is greater than a magnitude of the first stimulation pulse, and wherein sensing circuitry of the medical device is configured to sense the first stimulation pulse and to block sensing for the second stimulation pulse.

Example 7: The medical device of any combination of examples 1-6, wherein the value of the stimulation parameter comprises one or more of: a magnitude of current, a pulse width, and a pulse shape.

Example 8: The medical device of any combination of examples 1-7, wherein the stimulation generation circuitry is configured to deliver a plurality of stimulation pulses and wherein the sensing circuitry is further configured to: detect a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

Example 9: The medical device of any combination of examples 1-8, wherein the processing circuitry is further configured to determine whether the plurality of stimulation pulses elicit greater than a threshold ratio of detectable ECAPs per stimulation pulse.

Example 10: The medical device of any combination of examples 1-9, wherein to determine whether the plurality of stimulation pulses elicit greater than the threshold ratio of detectable ECAPs per stimulation pulse, the processing circuitry is configured to: identify a set of ECAPs elicited by a sequence of consecutive stimulation pulses of the plurality of stimulation pulses; calculate a ratio of a number of the set of ECAPs to a number of the sequence of consecutive stimulation pulses; and determine whether the ratio is greater than the threshold ratio.

Example 11: The medical device of any combination of examples 1-10, wherein the processing circuitry is further configured to: responsive to determining that the plurality of stimulation pulses elicit greater than the threshold ratio of detectible ECAPs: change, based on the value of the characteristic of the sensed first stimulation pulse and a value of a characteristic of an ECAP corresponding to the first stimulation pulse, the value of the parameter that at least partially defines the second stimulation pulse.

Example 12: The medical device of any combination of examples 1-11, wherein the processing circuitry is configured to trigger the respective pulse of the plurality of pulses to elicit a first ECAP of the plurality of ECAPS.

Example 13: The medical device of any combination of examples 1-12, wherein the event impacting therapy comprises a longitudinal lead migration, wherein to determine the occurrence of a longitudinal lead migration, the processing circuitry is configured to: determine a first value of one or more characteristics of the sensed delivered stimulation at a first time; determine a second value of one or more characteristics of a second sensed delivered stimulation at a second time; compare the first value to the second value; based on the comparison, determine whether a longitudinal lead migration has occurred.

Example 15: The medical device of any combination of examples 1-14, wherein the stimulation generation circuitry is configured to output the stimulation pulse to a first set of electrodes, wherein the sensing circuitry configured to sense the stimulation pulse from a second set of electrodes and sense the stimulation pulse from a third set of electrodes, and wherein the processing circuitry is configured to select one of the second set of electrodes or the third set of electrodes as the default sensing electrodes, based on: the value of one or more characteristics of the sensed delivered stimulation received from the second set of electrodes; and the value of one or more characteristics of the sensed delivered stimulation received from the third set of electrodes.

Example 16: The medical device of any combination of examples 1-15, wherein the processing circuitry is further configured to: communicate with an external computing device, output the one or more characteristics of the sensed delivered stimulation received from the second set of electrodes; and the one or more characteristics of the sensed delivered stimulation received from the third set of electrodes to the external computing device, and receive from the external computing device a selection of the default sensing electrodes.

Example 17: The medical device of any combination of examples 1-17, wherein the processing circuitry is further configured to: determine the occurrence of an event impacting therapy (EIT); responsive to the event impacting therapy, determine whether to take an action based on the event impacting therapy, responsive to determining to take the action, perform the action.

Example 18: The medical device of any combination of examples 1-16, wherein to perform the action comprises one or more of: store information regarding the event impacting therapy at a location of the memory, output an alert, control the stimulation generation circuitry to change one or more parameters of stimulation pulses of a plurality of stimulation pulses.

Example 19: The medical device of any combination of examples 1-18, further includes an accelerometer configured to generate an accelerometer signal, wherein the processing circuitry is further configured to: identify, based on the accelerometer signal, a posture of a set of postures which the patient is positioned; identify an amplitude of the first stimulation pulse; and select, based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

Example 20: The medical device of any combination of examples 1-19, wherein the medical device comprises an implantable medical device, and wherein the implantable medical device comprises the stimulation generation circuitry, the sensing circuitry, and the processing circuitry.

Example 21: A non-transitory computer-readable storage medium comprising instructions that, when executed, cause one or more processors of a computing device to perform the functions of examples 1-20.

Example 22: A method comprising: delivering, stimulation generation circuitry, electrical stimulation to a patient; sensing, by sensing circuitry the delivered electrical stimulation; determining, by processing circuitry operatively coupled to a memory, the value of one or more characteristics of the sensed delivered stimulation; and based on the value of the one or more characteristics of the sensed delivered stimulation, adjusting, by the processing circuitry, a stimulation parameter value that at least partially defines subsequent stimulation to be delivered to the patient.

Example 23: The method of example 22, wherein the electrical stimulation comprises an electrical current pulse.

Example 24: The method of any of examples 22 and 23, wherein the processing circuitry is configured to sense an event impacting therapy based on the value of the one or more characteristics of the sensed delivered stimulation.

Example 25: The method of example 24, wherein the event impacting therapy comprises one or more types, the types comprising an acute event, a periodic event, or other event.

Example 26: The method of examples 22-25, wherein: the acute event comprises: a patient cough, a patient sneeze, and a patient laugh; the periodic event comprises: the patient's breathing, and the patient sleeping; the other event comprises: the patient's posture change, a blood chemistry change; an electrode environment change, and a longitudinal lead movement.

Example 27: The method of any of examples 22-26, wherein the delivered electrical stimulation comprises a first stimulation pulse and a second stimulation pulse, wherein a magnitude of the second stimulation pulse is greater than a magnitude of the first stimulation pulse, the method further comprising sensing, by the sensing circuitry, the first stimulation pulse and blocking sensing for the second stimulation pulse.

Example 28: The method of any combination of examples 22-27, wherein the value of the stimulation parameter comprises one or more of: a magnitude of current, a pulse width, and a pulse shape.

Example 29: The method of any of examples 22-28, further comprising: delivering, by the stimulation generation circuitry, a plurality of stimulation pulses and detecting, by the sensing circuitry, a plurality of evoked compound action potentials (ECAPs), wherein each ECAP of the plurality of ECAPs is elicited by a respective pulse of the plurality of pulses, and wherein the number of ECAPs of the plurality of ECAPs is lower than a number of stimulation pulses of the plurality of stimulation pulses.

Example 30: The method of any of examples 22-29, further comprising determining, the processing circuitry, whether the plurality of stimulation pulses elicit greater than a threshold ratio of detectable ECAPs per stimulation pulse.

Example 31: The method of any of examples 22-30, wherein determining whether the plurality of stimulation pulses elicit greater than the threshold ratio of detectable ECAPs per stimulation pulse, comprises: identifying, by the processing circuitry, a set of ECAPs elicited by a sequence of consecutive stimulation pulses of the plurality of stimulation pulses; calculating a ratio of a number of the set of ECAPs to a number of the sequence of consecutive stimulation pulses; and determining whether the ratio is greater than the threshold ratio.

Example 32: The method of any of examples 22-31, further comprising: responsive to determining that the plurality of stimulation pulses elicit greater than the threshold ratio of detectible ECAPs: changing, by the processing circuitry the value of the parameter that at least partially defines the second stimulation pulse based on the value of the characteristic of the sensed first stimulation pulse and a value of a characteristic of an ECAP corresponding to the first stimulation pulse.

Example 33: The method of any of examples 22-32, further comprising triggering, by the processing circuitry, the respective pulse of the plurality of pulses to elicit a first ECAP of the plurality of ECAPS.

Example 34: The method of any of examples 22-33, wherein the event impacting therapy comprises a longitudinal lead migration, and wherein determining the occurrence of a longitudinal lead migration comprises: determining, by the processing circuitry, a first value of one or more characteristics of the sensed delivered stimulation at a first time; determining a second value of one or more characteristics of a second sensed delivered stimulation at a second time; comparing the first value to the second value; and based on the comparison, determining whether a longitudinal lead migration has occurred.

Example 35: The method of any of examples 22-34, wherein the stimulation generation circuitry is configured to output the stimulation pulse to a first set of electrodes, wherein the sensing circuitry configured to sense the stimulation pulse from a second set of electrodes and sense the stimulation pulse from a third set of electrodes, the method further comprising selecting, by the processing circuitry, one of the second set of electrodes or the third set of electrodes as the default sensing electrodes, based on: the value of one or more characteristics of the sensed delivered stimulation received from the second set of electrodes; and the value of one or more characteristics of the sensed delivered stimulation received from the third set of electrodes.

Example 36: The method of any of examples 22-35, further comprising, communicating, by the processing circuitry, with an external computing device, outputting the one or more characteristics of the sensed delivered stimulation received from the second set of electrodes; and the one or more characteristics of the sensed delivered stimulation received from the third set of electrodes to the external computing device, and receiving from the external computing device a selection of the default sensing electrodes.

Example 37: The method of any of examples 2-36, further comprising: determining, by the processing circuitry, the occurrence of an event impacting therapy (EIT); responsive to the event impacting therapy, determining whether to take an action based on the event impacting therapy, responsive to determining to take the action, performing the action.

Example 38: The method of any of examples 22-37, wherein to perform the action comprises one or more of: store information regarding the event impacting therapy at a location of the memory, output an alert, control the stimulation generation circuitry to change one or more parameters of stimulation pulses of a plurality of stimulation pulses.

Example 39: The method of any of examples 22-38, further comprising: receiving by the processing circuitry, an accelerometer signal generated by an accelerometer; identifying, based on the accelerometer signal, a posture of a set of postures which the patient is positioned; identifying an amplitude of the first stimulation pulse; and selecting, based on the identified posture and the amplitude of the first stimulation pulse, the target stimulation pulse value from a set of target stimulation pulse values, wherein each target stimulation pulse value of the set of target stimulation pulse values corresponds to a respective posture of the set of postures and a respective amplitude of the first stimulation pulse.

Example 40: The method of any of examples 22-39, wherein an implantable medical device comprises the stimulation generation circuitry, the sensing circuitry, and the processing circuitry.

Example 41: A medical device includes stimulation generation circuitry configured to deliver a first stimulation pulse to a patient; sensing circuitry configured to sense a residual phase of the first stimulation pulse; and processing circuitry configured to: determine that a value of a characteristic of the sensed residual phase of the first stimulation pulse exceeds a target residual phase value; and responsive to determining that the value of the characteristic of the sensed residual phase exceeds the target residual phase value, change a first value of a parameter to a second value of the parameter that at least partially defines a second stimulation pulse deliverable by the stimulation generation circuitry after the residual phase of the first stimulation pulse was sensed.

Various examples of the disclosure have been described. These and other examples are within the scope of the following claims.

What is claimed is:

1. A medical device comprising:
stimulation generation circuitry configured to deliver electrical stimulation to a patient;
sensing circuitry configured to sense the delivered electrical stimulation; and
processing circuitry operatively coupled to a memory, the processing circuitry configured to:
determine a value of one or more characteristics of the sensed delivered stimulation; and
based on the value of the one or more characteristics of the sensed delivered stimulation, adjust a value of a stimulation parameter that at least partially defines subsequent stimulation to be delivered to the patient,
wherein the stimulation generation circuitry is configured to output a stimulation pulse to a first set of electrodes,
wherein the sensing circuitry configured to sense the stimulation pulse via a second set of electrodes and sense the stimulation pulse via a third set of electrodes, and
wherein the processing circuitry is configured to select one of the second set of electrodes or the third set of electrodes as a default set of sensing electrodes, based on:
a value of one or more characteristics of the sensed stimulation pulse received from the second set of electrodes; and
a value of one or more characteristics of the sensed stimulation pulse received from the third set of electrodes.

2. The medical device of claim 1, wherein the electrical stimulation comprises an electrical current pulse.

3. The medical device of claim 1, wherein the processing circuitry is configured to sense an event impacting therapy (EIT) based on the value of the one or more characteristics of the sensed delivered stimulation.

4. The medical device of claim 3, wherein the event impacting therapy comprises one or more types, the types comprising an acute event, a periodic event, or other event.

5. The medical device of claim 4, wherein:
the acute event comprises: a cough, a patient, and a laugh of the patient;
the periodic event comprises: breathing and/or sleeping;
the other event comprises: a posture change of the patient, a blood chemistry change; an electrode environment change and a longitudinal lead movement.

6. The medical device of claim 1, wherein the delivered electrical stimulation comprises a first stimulation pulse and a second stimulation pulse,
wherein a magnitude of the second stimulation pulse is greater than a magnitude of the first stimulation pulse, and
wherein sensing circuitry of the medical device is configured to sense the first stimulation pulse and to block sensing for the second stimulation pulse.

7. The medical device of claim 1, wherein the value of the stimulation parameter comprises one or more of: a magnitude of current, a value of a pulse width, or a value of a pulse shape.

8. The medical device of claim 1, wherein the stimulation generation circuitry is configured to deliver a plurality of stimulation pulses and wherein the sensing circuitry is further configured to:
detect a plurality of evoked compound action potentials (ECAPs), wherein each ECAP of the plurality of ECAPs is elicited by a respective pulse of the plurality of pulses, and wherein a number of ECAPs of the plurality of ECAPs is lower than a number of stimulation pulses of the plurality of stimulation pulses.

9. The medical device of claim 6, wherein the processing circuitry is further configured to determine whether the plurality of stimulation pulses elicit greater than a threshold ratio of detectable ECAPs per stimulation pulse.

10. The medical device of claim 9, wherein to determine whether the plurality of stimulation pulses elicit greater than the threshold ratio of detectable ECAPs per stimulation pulse, the processing circuitry is configured to:
identify a set of ECAPs elicited by a sequence of consecutive stimulation pulses of the plurality of stimulation pulses;
calculate a ratio of a number of the set of ECAPs to a number of the sequence of consecutive stimulation pulses; and
determine whether the ratio is greater than the threshold ratio.

11. The medical device of claim 9, wherein the processing circuitry is further configured to:
responsive to determining that the plurality of stimulation pulses elicit greater than the threshold ratio of detectible ECAPs:
change, based on the value of the characteristic of the sensed delivered stimulation and a value of a characteristic of an ECAP corresponding to the sensed delivered stimulation, the value of the parameter that at least partially defines the second stimulation pulse.

12. The medical device of claim 8, wherein the processing circuitry is configured to trigger the respective pulse of the plurality of pulses to elicit a first ECAP of the plurality of ECAPS.

13. The medical device of claim 3,
wherein the event impacting therapy comprises a longitudinal lead migration,
wherein to determine the longitudinal lead migration, the processing circuitry is configured to:
determine a first value of one or more characteristics of the sensed delivered stimulation at a first time;

determine a second value of one or more characteristics of a second sensed delivered stimulation at a second time;

compare the first value to the second value; and based on the comparison, determine whether a longitudinal lead migration has occurred.

14. The medical device of claim 1, wherein the medical device is configured to:

deliver the electrical stimulation to the patient via an electrode mounted to a housing of the medical device; and sense a bioelectrical signal of the patient via the electrode mounted to the housing of the medical device.

15. The medical device of claim 1, wherein the processing circuitry is further configured to:

communicate with an external computing device, output the one or more characteristics of the sensed delivered stimulation received from the second set of electrodes to the external computing device;

output the one or more characteristics of the sensed delivered stimulation received from the third set of electrodes to the external computing device, and receive, from the external computing device, a selection of the default sensing electrodes.

16. A method comprising:

causing, by processing circuitry of a medical device, stimulation generation circuitry of the medical device to deliver electrical stimulation to a patient, wherein the processing circuitry is operatively coupled to a memory;

receiving, by the processing circuitry, an indication of the delivered electrical stimulation from sensing circuitry of the medical device that is configured to sense the delivered electrical stimulation;

determining, by the processing circuitry, a value of one or more characteristics of the sensed delivered stimulation;

based on the value of the one or more characteristics of the sensed delivered stimulation, adjusting, by the processing circuitry, a value of a stimulation parameter that at least partially defines subsequent stimulation to be delivered to the patient outputting, by the stimulation generation circuitry, stimulation pulse to a first set of electrodes;

sensing, by the sensing circuitry, the stimulation pulse via a second set of electrodes;

sensing, by the sensing circuitry, the stimulation pulse via a third set of electrodes;

selecting, by the processing circuitry, one of the second set of electrodes or the third set of electrodes as a default set of sensing electrodes, based on:

a value of one or more characteristics of the sensed stimulation pulse received from the second set of electrodes; and a value of one or more characteristics of the sensed stimulation pulse received from the third set of electrodes.

17. The method of claim 16, further comprising, detecting an event impacting therapy (EIT) based on the value of the one or more characteristics of the sensed delivered stimulation.

18. The method of claim 17, further comprising:

responsive to detecting the event impacting therapy, determining to take an action based on the event impacting therapy; and responsive to determining to take the action, performing the action by one or more of: storing information regarding the event impacting therapy at a location of the memory, outputting an alert, or controlling the stimulation generation circuitry to change one or more parameters of stimulation pulses of a plurality of stimulation pulses.

19. The method of claim 16, further comprising:

delivering, by the stimulation generation circuitry, a plurality of stimulation pulses;

detecting, by the sensing circuitry, a plurality of evoked compound action potentials (ECAPs), wherein each ECAP of the plurality of ECAPs is elicited by a respective pulse of the plurality of pulses, and wherein a number of ECAPs of the plurality of ECAPs is lower than a number of stimulation pulses of the plurality of stimulation pulses;

determining that the plurality of stimulation pulses elicit greater than a threshold ratio of detectable ECAPs per stimulation pulse; and responsive to determining that the plurality of stimulation pulses elicit greater than the threshold ratio of detectible ECAPs, changing, based on the value of the characteristic of the sensed delivered stimulation and a value of a characteristic of an ECAP corresponding to the sensed delivered stimulation, the value of the parameter that at least partially defines the second stimulation pulse.

20. A non-transitory computer-readable storage medium comprising instructions that, when executed, causes processing circuitry:

control stimulation generation circuitry of a medical device to deliver electrical stimulation to a patient, wherein the processing circuitry is operatively coupled to a memory;

receive an indication of the delivered electrical stimulation sensed by from sensing circuitry of the medical device that is configured to sense the delivered electrical stimulation;

determine a value of one or more characteristics of the sensed delivered stimulation;

adjust, based on the value of the one or more characteristics of the sensed delivered stimulation, a value of a stimulation parameter that at least partially defines subsequent stimulation to be delivered to the patient;

control the stimulation generation circuitry to output a stimulation pulse to a first set of electrodes, control sensing circuitry to sense the stimulation pulse via a second set of electrodes and sense the stimulation pulse via a third set of electrodes, and select one of the second set of electrodes or the third set of electrodes as a default set of sensing electrodes, based on:

a value of one or more characteristics of the sensed stimulation pulse received from the second set of electrodes; and a value of one or more characteristics of the sensed stimulation pulse received from the third set of electrodes.

* * * * *